US009717744B2

(12) United States Patent
DeLuca et al.

(10) Patent No.: US 9,717,744 B2
(45) Date of Patent: *Aug. 1, 2017

(54) USE OF 2-METHYLENE-19-NOR-(20S)-1α,25-DIHYDROXYVITAMIN D3 TO PREVENT SECONDARY HYPERPARATHYROIDISM OR THE SYMPTOMS THEREOF

(71) Applicant: Wisconsin Alumni Research Foundation, Madison, WI (US)

(72) Inventors: Hector F. DeLuca, Deerfield, WI (US); Lori A. Plum, Arena, WI (US); Julia B. Zella, Horicon, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/947,142

(22) Filed: Nov. 20, 2015

(65) Prior Publication Data

US 2016/0136184 A1    May 19, 2016

Related U.S. Application Data

(63) Continuation of application No. 13/828,090, filed on Mar. 14, 2013, now Pat. No. 9,205,096.

(60) Provisional application No. 61/666,264, filed on Jun. 29, 2012.

(51) Int. Cl.
*A61K 31/593* (2006.01)

(52) U.S. Cl.
CPC .................................. *A61K 31/593* (2013.01)

(58) Field of Classification Search
None
See application file for complete search history.

(56) References Cited

U.S. PATENT DOCUMENTS

| 5,843,928 | A | 12/1998 | Deluca et al. |
|---|---|---|---|
| 6,136,799 | A | 10/2000 | Li et al. |
| 7,563,783 | B2 | 7/2009 | DeLuca et al. |
| 2002/0028830 | A1 | 3/2002 | Deluca et al. |
| 2005/0124591 | A1 | 6/2005 | Tian et al. |
| 2005/0187201 | A1 | 8/2005 | DeLuca et al. |
| 2006/0003973 | A1 | 1/2006 | DeLuca et al. |
| 2006/0135492 | A1 | 6/2006 | DeLuca et al. |
| 2006/0171983 | A1 | 8/2006 | Tian et al. |
| 2010/0087404 | A1 | 4/2010 | Mazess et al. |
| 2011/0034426 | A1 | 2/2011 | Deluca et al. |

FOREIGN PATENT DOCUMENTS

| JP | 2002543115 | 12/2002 |
|---|---|---|
| JP | 2003528833 | 9/2003 |
| JP | 2007508298 | 4/2007 |
| JP | 2007523162 | 8/2007 |
| WO | 0066098 | 11/2000 |
| WO | 0172292 | 10/2001 |
| WO | 0205823 | 1/2002 |
| WO | 2005039592 | 5/2005 |
| WO | 2005082456 | 9/2005 |
| WO | 2009/026265 A1 | 2/2009 |
| WO | 2011119610 | 9/2011 |

OTHER PUBLICATIONS

Advisory Action for U.S. Appl. No. 12/845,173 dated Aug. 28, 2014.
Advisory Action for U.S. Appl. No. 12/845,173 dated Oct. 21, 2013.
Barycki et al., "Removal of the 20-methyl group from 2-methylene-19-nor-(20S)-1alpha,25-dihydroxyvitamin D(3) (2MD) selectively eliminates bone calcium mobilization activity," Bioorg Med Chem., Nov. 15, 2009, 17(22):7658-69.
Bradford, Marion M., "A Rapid and Sensitive Method for the Quantitation of Microgram Quantities of Protein Utilizing the Principle of Protein-Dye Binding", Analytical Biochemistry, 1976, 72: 248-254.
Brown et al., "The Noncalcemic Analogue of Vitamin D, 22-Oxacalcitriol, Suppresses Parathyroid Hormone Synthesis and Secretion", J. Clin. Invest, 1989, 84: 728-732.
Chen et al, "Modulatory Effects of 1,25-Dihydroxyvitamin D3 on Human B Cell Differentiation", The Journal of Immunology, 2007, 179: 1634-1647.
Darwish et al., "Identification of a Transcription Factor That Binds to the Promoter Region of the Human Parathyroid Hormone Gene", Archives of Biochemistry and Biophysics, 1999, 365(1): 123-130.
Declaration for U.S. Appl. No. 12/845,173 dated Sep. 27, 2011.
Deluca, "The development of a bone- and parathyroid-specific analog of vitamin D: 2-methylene-19-Nor-(20S)-1alpha,25-dihydroxyvitamin D3," Bonekey Rep, Mar. 5, 2014, 2:514.
Deluca et al., "The vitamin D analogue 2MD increases bone turnover but not BMD in postmenopausal women with osteopenia: results of a 1-year phase 2 double-blind, placebo-controlled, randomized clinical trial," J Bone Miner Res., Mar. 2011, 26(3):538-545.
Deluca et al., "Vitamin D: The Vitamin and the Hormone", Fed. Proc., 1974, 33: 2211-2219.
DeLuca H.F. "Therapeutic potential of the 2-aklyl and 2-alkylidene-19-nor-(20S)-odified analogs of 1-25-dihydroxyvitamin D3." Journal of Steroid Biochemistry & Molecular Biology 89-90 (2004) 67-73.

(Continued)

*Primary Examiner* — Sreeni Padmanabhan
*Assistant Examiner* — Jody Karol
(74) *Attorney, Agent, or Firm* — Andrus Intellectual Property Law, LLp

(57) ABSTRACT

Disclosed are methods of administering 2-methylene-19-nor-(20S)-1α,25-dihydroxyvitamin $D_3$ to treat and/or prevent secondary hyperparathyroidism and/or its accompanying symptoms in a subject having or at risk for developing secondary hyperparathyroidism.

7 Claims, 13 Drawing Sheets

(56) References Cited

OTHER PUBLICATIONS

Delmez, et al., "Hyperphosphatemia: Its Consequences and Treatment in Patients with Chronic Renal Disease", American Journal of Kidney Diseases, 1992, XIX(4): 303-317.
Demay et al., "Sequences in the Human Parathyroid Hormone Gene that Bind the 1,25-Dihydroxyvitamin D3 Receptor and Mediate Transcriptional Repression in Response to 1,25-Dihydroxyvitamin D3", Proc. Natl. Acad. Sci. USA, 1992, 89: 8097-8101.
Final Office Action for U.S. Appl. No. 12/845,173 dated Jul. 3, 2013.
Final Office Action for U.S. Appl. No. 12/845,173 dated Mar. 31, 2014.
International Preliminary Report on Patentability for PCT/US2010/043551 dated Feb. 16, 2012.
International Search Report and Written Opinion, PCT International Application No. PCT/US2013/031574, mailed Apr. 25, 2013.
International Search Report and Written Opinion in PCT/US2010/043551, filed Jul. 28, 2010.
Ke et al., "A New Vitamin D Analog, 2MD, Restores Trabecular and Cortical Bone Mass and Strength in Ovariectomized Rats With Established Osteopenia", Journal of None and Mineral Research, 2005, 20: 1742-1755.
Kim, James, "Effects of 1α,25-dihydroxyvitamin D3 on the MRL/MpJ-fas/lpr Model of Systemic Lupus Erythematosus", Ph.D. Thesis, University of Wisconsin-Madison, 2009.
Komaba et al. "Diseases of the parathyroid gland in chronic kidney disease". Clin Exp Nephrol (2011) 15:797-809.
Lopez-Hilker, et al., "Phosphorus Restriction Reverses Hyperparathyriodism in Uremia Independent of Changes in Calcium and Calcitriol", American Journal of Physiology—Renal Physiology, 1990, 259: 432-437.
Meyrier et al., "The Influence of High Calcium Carbonate Intake on Bone Disease in Patients Undergoing Hemodialysis", Kidney International, 1973, 4: 146-153.
Moriniere, et al., "Subtitution of Aluminium Hydroxide by High Doses of Calcium Carbonate in Patients on Chronic Haemodialysis: Disappearance of Hyperaluminaemia and Equal Control of Hyperparathyriodism", Proc. EDTA, 1982, 19: 784-787.
National Kidney Foundation, Inc. Part 4. Definition and Classification of Stages of Kidney Disease, American Journal of Kidney Diseases, vol. 39, No. 2, Suppl 1. Feb. 2002, pp. S46-S75.
Office Action for U.S. Appl. No. 12/845,173 dated Aug. 24, 2012.
Office Action for JP2012-523654 dated Aug. 29, 2014.
Office Action for U.S. Appl. No. 12/845,173 dated Nov. 6, 2014.
Portale, et al., "Effect of Dietary Phosphorus on Circulating Concentrations of 1,25-Dihydroxyvitamin D and Immunoreactive Parathyroid Hormone in Children with Moderate Renal Insufficiency", J. Clin. Invest., 1984, 73: 1580-1589.
Quarles, et al., "Prospective Trial of Pulse Oral Intravenous Calcitriol Treatment of Hyperparathyriodism in ESRD", Kidney International, 1994, 45: 1710-1721.
Response for U.S. Appl. No. 12/845,173 dated Apr. 6, 2015.
Response for U.S. Appl. No. 12/845,173 dated Jul. 25, 2014.
Response for U.S. Appl. No. 12/845,173 dated Nov. 4, 2013.
Response for U.S. Appl. No. 12/845,173 dated Oct. 2, 2013.
Response for U.S. Appl. No. 12/845,173 dated Jan. 23, 2013.
Sato et al., "New 19-nor-(20S)-1alpha,25-dihydroxyvitaimin D3 analogs strongly stimulate osteoclast formation both in vivo and in vitro," Bone, Feb. 2007, 40(2):293-304.
Search Report for SG11201408731W dated Jun. 23, 2015.
Shevde et al., "A potent analog of 1alpha,25-dihydroxyvitamin D3 selectively induces bone formation", PNAS, 2002, 99(21): 13487-13491.
Sibilska et al., "1-desoxy analog of 2MD: synthesis and biological activity of (20S)-25-hydroxy-2-methylene-19-norvitamin D3," J Steroid Biochem Mol Bio, Jul. 2010, 121(1-2):51-55.
Slatopolsky et al., "New analog of calcitriol, 19-nor-1,25-(OH)2D2, suppresses parathyroid hormone secretion in uremic rats in the absence of hypercalcemia," American Journal of Kidney Diseases, Nov. 1995, 26(5):852-860.
Slatopolsky et al., "Marked Suppression of Secondary Hyperparathyroidism by Intravenous Administration of 1,25-Dihydroxycholecalciferol in Uremic Patients", J. Clin. Invest., 1984, 74: 2136-2143.
Slatopolsky et al., "Calcium Carbonate as a PHosphate Binder in Patients with Chronic Renal Failure Undergoing Dialysis", New Engl. J. Med., 1986, 315: 157-161.
U.S. Appl. No. 09/616,164, filed Jul. 14, 2000.
Written Opinion for SG11201408731W dated Aug. 14, 2015.
Vanhooke et al., "New analogs of 2-methylene-19-nor-(20S)-1,25-dihydroxyvitamin D3 with conformationally restricted side chains: evaluation of biological activity and structural determination of VDR-bound conformations," Arch Biochem Biophys, Apr. 15, 2007, 460(2):161-165.
Yamamoto et al, "2-Methylene-19-nor-(20S)-1alpha,25-dihydroxyvitamin D3 Potently Stimulates Gene-specific DNA Binding of the Vitamin D Receptor in Osteoblasts", Journal of Biological Chemistry, 2003, 278(34): 31756-31765.
Zella et al., "2MD, a Potent and Selective 1,25-Dihydroxyvitamin D Analog, Suppresses PTH in 5/6-Nephrectomized Rats and in Post-menopausal Women", American Journal of Nephrology, Mar. 6, 2014, pp. 1-50.
Khan, et al., "Primary hyperparathyroidism: pathophysiology and impact on bone", CMAJ (2000); 163(2): 184-187.

Fig. 4 Uremic Rat Model - Oral

Endpoints: Blood collected at baseline and termination for serum PTH (Intact PTH ELISA from Immutopics) and calcium (atomic absorption) measurements.

Fig. 5 PTH

USE OF 2-METHYLENE-19-NOR-(20S)-1α,25-DIHYDROXYVITAMIN D3 TO PREVENT SECONDARY HYPERPARATHYROIDISM OR THE SYMPTOMS THEREOF

CROSS-REFERENCE TO RELATED PATENT APPLICATIONS

The present application is a continuation of U.S. application Ser. No. 13/282,090, filed on Mar. 14, 2013, which claims the benefit of priority under 35 U.S.C. §119(e) to U.S. Provisional Patent Application No. 61/666,264, filed on Jun. 29, 2012, the contents of which are incorporated herein by reference in their entireties.

BACKGROUND

This invention relates to vitamin D compounds useful in treating and/or preventing secondary hyperparathyroidism and/or the symptoms thereof, and more particularly to the use of the vitamin D compound 2-methylene-19-nor-(20S)-1α,25-dihydroxyvitamin D3 to treat and/or prevent secondary hyperparathyroidism and/or the symptoms thereof.

Renal disease has become an increasingly important health problem in virtually every country in the world including highly developed countries such as the United States. Presently there are about 250,000 patients on renal dialysis who have lost almost complete use of their kidneys. There are approximately ten times this number of patients who have lost some degree of renal function due to renal disease and are progressing, to complete renal failure. Renal failure is evidenced by a decreased glomeruli filtration rate (GFR) from a high value of 110 ml/minute/1.73 m$^2$ to 30 ml/minute/1.73 m$^2$ where dialysis is often initiated.

Many factors contribute to the development of renal disease. High blood pressure is one of the significant contributors, as is having Type I or Type II diabetes. Current treatments for renal failure are limited to hemodialysis, an extremely expensive procedure that currently is supported by federal governments because individuals typically cannot afford this procedure on their own. The annual cost of renal disease in the United States alone is over $42 billion. Accordingly, effective methods for preventing renal disease and treating symptoms thereof would not only provide a major health benefit but would also provide a major economic benefit.

It is now universally accepted that vitamin D must first be 25-hydroxylated in the liver and subsequently 1α-hydroxylated in the kidney before it can function. (See DeLuca, "Vitamin D: The vitamin and the hormone," Fed. Proc. 33, 2211-2219, 1974). These two reactions produce the final active form of vitamin D, namely 1α,25-(OH)$_2$D$_3$. (See DeLuca & Schnoes, "Vitamin D; Recent advances," Ann. Rev. Biochem. 52, 411-439, 1983). This compound then stimulates a number of physiological processes including: stimulating the intestine to absorb calcium, stimulating the kidney to reabsorb calcium, stimulating the intestine to absorb phosphate, and stimulating, bone to mobilize calcium when signaled by high parathyroid hormone (PTH) levels. These actions result in a rise in plasma calcium and phosphorus levels that bring about the healing of bone lesions such as rickets and osteomalacia and prevent the neurological disorder of hypocalcemic tetany.

Secondary hyperparathyroidism is a universal complication in patients with chronic renal failure. Low levels of 1α,25-(OH)$_2$D$_3$ and phosphate retention are responsible for the development of secondary hyperparathyroidism. Low levels of circulating 1α,25-(OH)$_2$D$_3$ are the result of impaired kidney function resulting in the patient's inability to convert 25-hydroxy-vitamin D$_3$ to 1α,25-dihydroxyvitamin D$_3$. As a result of low levels of circulating 1α,25-(OH)$_2$D$_3$, intestinal calcium absorption is minimal which subsequently results in insufficient serum calcium levels. When the parathyroid glands sense a low level of serum calcium, the parathyroid glands secrete PTH which causes calcium to be mobilized from bone to regulate serum calcium. Left unchecked, this abnormal secretion of PTH will lead to the development of renal osteodystrophy. High PTH levels can also lead to: 1) weakening, of the bones; 2) calciphylaxis (when calcium forms clumps in the skin and lead to ulcers and potentially death of surrounding tissue); 3) cardiovascular complications; 4) abnormal fin and sugar metabolism; 5) itching (pruritis); and 6) low blood counts (anemia).

1α,25-dihydroxyvitamin D$_3$ has been used as a therapeutic for hyperparathyroidism in patients with renal diseases. In the treatment of secondary hyperparathyroidism of renal osteodystrophy, it is well known that 1α,25-dihydroxyvitamin D$_3$ binds to the vitamin D receptor (VDR) located in the parathyroid glands to suppress both growth and proliferation of the parathyroid cells and expression of the preproparathyoid gene. (See Demay et al., "Sequences in the human parathyroid hormone gene that bind the 1,25-dihydroxyvitamin D$_3$ receptor and mediate transcriptional repression in response to 1,25-hydroxyvitamin D$_3$." Proc. Natl. Acad. Sci. USA 89, 8097-8101, 1992; and Darwish & DeLuca, "Identification of a transcription factor that binds to the promoter region of the human parathyroid hormone gene," Arch. Biochem. Biophys. 355, 123-130, 1999). Because of its ability to suppress parathyroid hormone (PTH), 1,25-(OH)$_2$D$_3$ has been used with success in the treatment of secondary hyperparathyroidism. (See Slatopolsky et al., "Marked Suppression of Secondary Hyperparathyroidism by Intravenous Administration of 1,25-dihydroxycholecalciferol in Uremic Patients," J. Clin. Invest. 74:2136-2143, 1984). The use of 1α,25-dihydroxyvitamin D$_3$ in the treatment of secondary hyperparathyroidism of renal osteodystrophy is often precluded, however, by the development of hypercalcemia resulting from 1α,25-dihydroxyvitamin D$_3$'s potent action on intestinal calcium absorption and bone mineral calcium mobilization.

As noted previously, secondary hyperparathyroidism typically will occur in patients undergoing renal dialysis. Chronic renal failure is the most common cause of secondary hyperparathyroidism. Failing kidneys do not convert enough vitamin D to its active form and do not adequately excrete phosphate. When this happens, insoluble calcium phosphate forms in the body and removes calcium from circulation. Ultimately, this leads to hypocalcemia and secondary hyperparathyroidism.

Secondary hyperparathyroidism also can result from gastrointestinal malabsorption syndromes (e.g., chronic pancreatitis, small bowel disease, and malabsorption-dependent bariatric surgery in which the intestines do not absorb vitamins and minerals properly), where these syndromes may result in insufficient, absorption of the fat soluble vitamin D. When vitamin D is insufficiently absorbed, hypocalcemia may develop and a subsequent increase in PTH secretion may result where the body attempts to increase serum calcium levels. However, hypocalcemia and secondary hyperparathyroidism also may appear in the early stages of renal disease due to low levels of 1,25(OH)$_2$D$_3$. Other less common causes of secondary hyperparathyroidism are long-term lithium therapy, vitamin D deficiency, malnutrition, vitamin D-resistant rickets, or hypermagnesemia (i.e., abnormally high blood magnesium levels).

Symptoms of secondary hyperparathyroidism include increased, levels of serum PTH, serum phosphorus, and serum creatinine. Less overt symptoms include bone and joint pain, bone deformities, broken bones (fractures), swollen joints, kidney stones, increased urination, muscle weakness and pain, nausea, and loss of appetite. Other less common symptoms include fatigue, upper abdominal pain, and depression.

Treatment of secondary hyperparathyroidism typically involves addressing the underlying cause of the hypocalcemia. In patients with chronic renal failure, treatment consists of dietary restriction of phosphorus, supplements with an active form of vitamin D such as calcitriol, Hectorol®, or Zemplar®(paricalcitol), and phosphate binders which can be divided into calcium-based binders and non-calcium based binders. A newer class of medication is calcimimetics, one of which is commercially available as Sensipar®(cinacalcet) in the United States and Australia, and as Mimpara® in the European Union. Calcimimetics have achieved positive responses and are FDA approved for use in patients on dialysis, but have not been approved for use in chronic kidney disease pre-dialysis because, among other concerns, they can increase phosphorus levels. Most patients with hyperparathyroidism secondary to chronic kidney disease will improve after renal transplant, but many will continue to have a degree of residual hyperparathyroidism (i.e., tertiary hyperparathyroidism) post-transplant with associated risk of bone loss.

Although serum phosphorus is usually normal in patients with early renal insufficiency, phosphate restriction can reduce secondary hyperparathyroidism. Dietary phosphate restriction increases $1,25\text{-}(OH)_2D_3$ levels. (See Portale et al., "Effect of Dietary Phosphorus on Circulating Concentrations of 1,25-dihydroxyvitamin D and Immunoreactive Parathyroid Hormone in Children with Moderate Renal Insufficiency," J. Clin. Invest. 73:1580-1589, 1984). This in turn decreases PTH by directly suppressing PTH gene transcription and by increasing intestinal calcium absorption. In later stages of renal failure, the extent of hyperparathyroidism and $1,25\text{-}(OH)_2D_3$ deficiency increases, and phosphate restriction has little effect on $1,25\text{-}(OH)_2D_3$ levels. (See Lopez-Hilker et al., "Phosphorus Restriction Reverses Hyperparathyroidism in Uremia Independent of Changes in Calcium and Calcitriol," Am. J. Physiol. 259: F432-F437, 1990). This is presumably due to the decreased renal mass available for $1,25\text{-}(OH)_2D_3$ synthesis.

Several vitamin D analogs with low calcemic activity have been found to be nearly as effective as $1,25\text{-}(OH)_2D_3$ in suppressing PTH secretion by cultured bovine parathyroid cells. These include 22-oxacalcitriol (OCT), (Brown et al., "The Non-Calcemic Analog of Vitamin D, 22-oxacalcitriol (OCT) Suppresses Parathyroid Hormone Synthesis and Secretion," J. Clin. Invest. 84:728-732, 1989), as well as $1,25\text{-}(OH)_2\text{-}16\text{-ene-}23\text{-yne-}D_3$, $1,25\text{-}(OH)_2\text{-}24\text{-dihomo-}D_3$, and $1,25\text{-}(OH)_2\text{-}24\text{-trihomo-}22\text{-ene-}D_3$. 22-oxacalcitriol has been examined in detail for this action in vivo. (See Brown et al., "Selective Vitamin U Analogs and their Therapeutic Applications," Sem. Nephrol 14:156-174, 1994, reporting that 22-oxacalcitriol, despite its rapid clearance in vivo, could suppress PTH mRNA). Low, submaximal doses of calcitriol and OCT exhibited comparable inhibition. OCT also has been shown to suppress serum PTH in uremic rats and dogs.

Another analog of $1,25\text{-}(OH)_2D_3$ with low calcemic and phosphatemic action is $19\text{-nor-}1,25\text{-}(OH)_2D_2$. This analog of calcitriol has the carbon 28 and the double bond at carbon 22 that are characteristic of vitamin $D_2$ compounds, but it lacks carbon 19 and the exocyclic double bond found in all natural vitamin D compounds. Studies in vitro utilizing a primary culture of bovine parathyroid cells demonstrated that $19\text{-nor-}1,25\text{-}(OH)_2D_2$ had a similar suppressive effect on PTH as $1,25\text{-}(OH)_2D_3$. A 52% suppression on PTH release was obtained with $19\text{-nor-}1,25\text{-}(OH)_2D_2$ at $10^{-7}$M. There was no significant difference in the suppressive effect of PTH secretion between the two compounds.

Thereafter, preliminary studies were performed in vivo to determine the calcemic activity of $19\text{-nor-}1,25\text{-}(OH)_2D_2$. It was found that $1,25\text{-}(OH)_2D_3$ (10 ng/rat/10 days) increased serum calcium to the same magnitude as $19\text{-nor-}1,25\text{-}(OH_2)D_2$ (100 ng/rat/10 days). Because of this, three different doses of $1,25\text{-}(OH)_2D_3$ (2, 4, and 8 ng) and $19\text{-nor-}1,25\text{-}(OH)_2D_2$ (8, 25, and 75 ng) were selected for chronic studies. After two months of renal insufficiency, the animals received the above two compounds at the three indicated doses, four times, during a period of eight days. As expected, $1,25\text{-}(OH)_2D_3$ suppressed pre-pro-PTH mRNA and PTH secretion. However, this decrease was statistically significant only with a 8 ng dose, and this dose induced hypercalcemia and hyperphosphatemia. On the other hand, none of the doses of $19\text{-nor-}1,25\text{-}(OH)_2D_2$ produced statistically significant changes in serum ionized calcium or serum phosphorus.

$19\text{-nor-}1\alpha,25(OH)_2D_2$ is also known as Paricalcitol and $19\text{-nor-}1\alpha,25\text{-dihydroxy-ergocalciferol}$. Paricalcitol injection is available commercially as Zemplar® from Abbott Laboratories, Abbott Park, Ill. A paricalcitol (Zemplar®) injection is described in U.S. Pat. No. 6,136,799 and has been approved by the FDA and is marketed for the prevention and treatment of secondary hyperparathyroidism associated with chronic renal failure (CKD Stage 5 or end-stage renal disease (ESRD), GFR <15 mL/min/1.73 $m^2$). This intravenous formulation contains 2-10 micrograms/milliliter of paricalcitol, 30% (viv) propylene glycol, 20% (v/v) ethanol and approximately 50% (v/v) water. Studies indicate that paricalcitol injection suppresses elevated levels of PTH with minimal effect on serum calcium and phosphorus levels. Since its approval by the FDA in April of 1998, it is estimated that approximately 200,000 patients have received at least one dose of paricalcitol injection. Clinically, the safety and efficacy of paricalcitol injection to treat secondary hyperparathyroidism are well established.

Hyperphosphatemia is also a persistent problem in chronic hemodialysis patients and can be further aggravated by therapeutic doses of $1,25\text{-}(OH)_2D_3$. (See Delmez et al., "Hyperphosphatemia: Its Consequences and Treatment in Patients with Chronic Renal Disease," Am. J. Kidney Dis. 19:303-317, 1992; and Quarks et al., "Prospective trial of Pulse Oral versus Intravenous Calcitriol Treatment of Hyperparathyroidism in ESRD," Kidney Int. 45:1710-1721, 1994). In addition, the control of phosphate absorption with large doses of calcium carbonate only increases the risk of hypercalcemia from $1,2\text{-}(OH)_2D_3$ therapy. (See Meyrier et al., "The Influence of a High Calcium Carbonate Intake on Bone Disease in Patients undergoing Hemodialysis," Kidney Int. 4:146-153, 1973; Moriniere of al., "Substitution of Aluminum Hydroxide by High Doses of Calcium Carbonate in Patients on Chronic Hemodialysis: Disappearance of Hyperaluminaemia and Equal Control of Hyperparathyroidism," Proc. Eur. Dial Transplant Assoc. 19:784-787, 1983; and Slatopolsky et al., "Calcium Carbonate as a Phosphate Binder in Patients with Chronic Renal Failure Undergoing Dialysis," New Engl. J. Med. 315:157-161, 1986). Thus, an analog of 1,25-$(OH)_2D_3$ that can suppress PTH with minor effects on calcium and phosphate metabolism would be an ideal tool for the control and treatment of secondary hyperparathyroidism.

Another vitamin D analog, namely, 2-methylene-19-nor-(20S)-1α,25-dihydroxyvitamin $D_3$ (referred to in the literature as "2MD") is also known to suppress PTH production. (See U.S. Published Application No. 2011/0034426A1). Although it would therefore appear to be a candidate for treating secondary hyperparathyroidism, it is also well known from U.S. Pat. No. 5,843,928 that 2MD has very potent calcemic activity. 2MD significantly increases bone calcium mobilization activity to a level likely to be 10-100 times that of 1α,25-$(OH)_2D_3$ while also exhibiting a modest increase in intestinal calcium transport activity. Due to this highly selective activity for the mobilization of calcium from hone, the compound 2MD was never seriously considered as a pharmaceutical agent for treating secondary hyperparathyroidism until now.

SUMMARY

It has now been discovered that the vitamin D analog 2MD has the ability to treat secondary hyperparathyroidism as well as symptoms of secondary hyperparathyroidism when administered under well-controlled conditions to a subject in need thereof. It also now been discovered that the vitamin D analog 2MD has the ability to prevent secondary hyperparathyroidism as well as symptoms of secondary hyperparathyroidism when administered under well-controlled conditions to a subject in need thereof.

In one embodiment, the present invention provides a novel method of treating secondary hyperparathyroidism by administering a therapeutically effective amount of a composition comprising 2-methylene-19-nor-(20S)-1α,25-dihydroxyvitamin $D_3$ (2MD) or pharmaceutically acceptable salts thereof as the active agent to a subject exhibiting symptoms of secondary hyperparathyroidism, without inducing hypercalcemia in the subject.

In another embodiment, the present invention provides a novel method of treating symptoms of secondary hyperparathyroidism by administering a therapeutically effective amount of a composition comprising 2-methylene-19-nor-(20S)-1α,25-dihydroxyvitamin $D_3$ (2MD) or pharmaceutically acceptable salts thereof as the active agent to a subject exhibiting symptoms of secondary hyperparathyroidism, without inducing hypercalcemia in the subject.

In yet another embodiment, the present invention provides a novel method of preventing secondary hyperparathyroidism by administering a therapeutically effective amount of a composition comprising 2-methylene-19-nor-(20S)-1α,25-dihydroxyvitamin $D_3$ (2MD) or pharmaceutically acceptable salts thereof as the active agent to a subject at risk of developing secondary hyperparathyroidism, without inducing hypercalcemia in the subject.

In still another embodiment, the present invention provides a novel method of preventing symptoms of secondary hyperparathyroidism by administering a therapeutically effective amount of a composition comprising of 2-methylene-19-nor-(20S)-1α,25-dihydroxyvitamin $D_3$ (2MD) or pharmaceutically acceptable salts thereof as the active agent to a subject at risk of developing secondary hyperparathyroidism, without inducing hypercalcemia in the subject.

In one embodiment, the 2-methylene-19-nor-(20S)-1α,25-dihydroxyvitamin D is formulated in an oral, topical, transdermal, parenteral, injectable or infusable form to be administered, in amounts ranging from 10 ng/day to about 1 µg/day. Preferably, for the treatment of or prevention of secondary hyperparathyroidism, or for the treatment or prevention of the symptoms of secondary hyperparathyroidism, the compound 2MD is administered either orally or parenterally (i.v.). The dose may be properly selected in accordance with the specific route of administration. Suitable doses may include doses within the range of about 10 ng to about 1 ug per day. Preferably a dose is administered three times per week either intravenously or orally to subjects receiving hemodialysis treatment.

DETAILED DESCRIPTION

Figure 1:
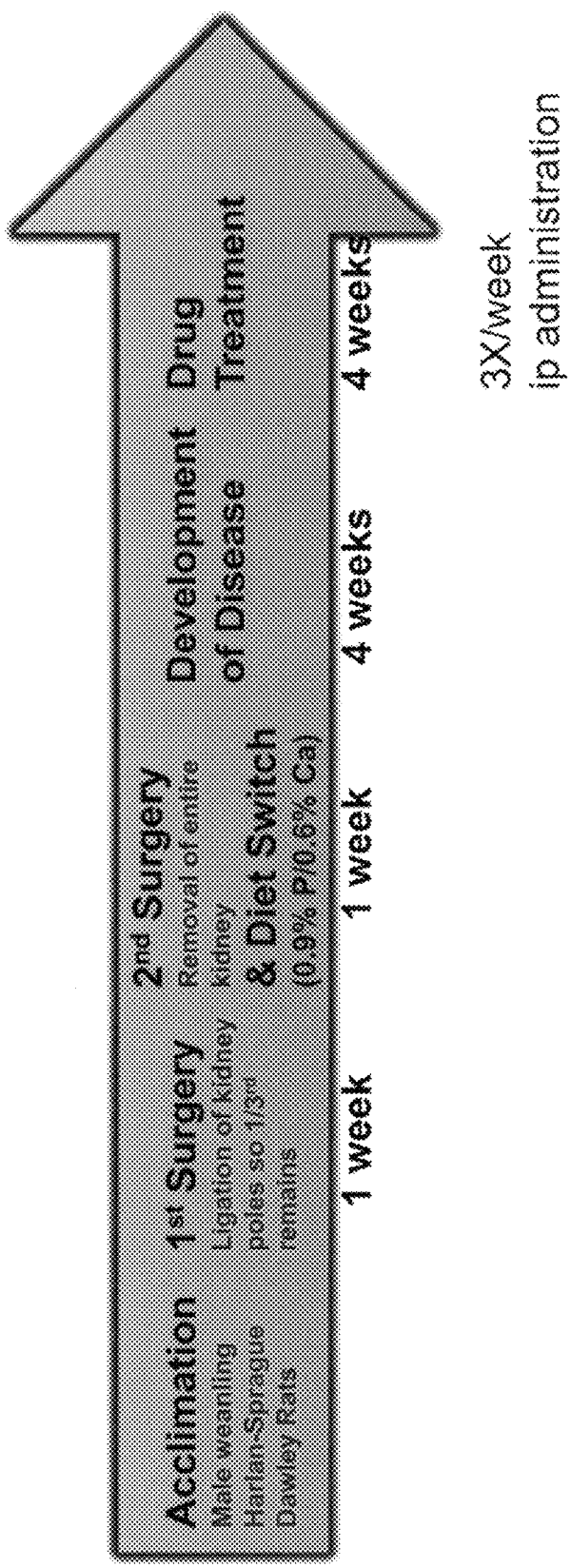
FIG. 1 schematically illustrates the intraperitoneal treatment protocol with 2MD contemplated herein.

Disclosed are methods of treating and/or preventing secondary hyperparathyroidism or the symptoms thereof. The disclosed methods further may described as follows based on the following definitions.

Unless defined otherwise, all technical and scientific terms used herein have the same meanings as commonly understood by one of ordinary skill in the art to Which this invention belongs. All publications and patents specifically mentioned herein are incorporated by reference in their entirety for all purposes including describing and disclosing the chemicals, instruments, statistical analyses and methodologies which are reported in the publications Which might be used in connection with the invention. All references cited in this specification are to be taken as indicative of the level of skill in the art. Nothing herein is to be construed as an admission that the invention is not entitled to antedate such disclosure by virtue or prior invention.

In the specification and in the claims, the terms "including" and "comprising" are open-ended terms and should be interpreted to mean "including, but not limited to." These terms encompass the more restrictive terms "consisting essentially of" and "consisting of." It is also to be noted that the terms "comprising," "including," "characterized by" and "having" can be used interchangeably.

As used herein and in the appended claims, the singular forms "a," "an," and "the" include plural reference unless the context clearly dictates otherwise. As well, the terms "a" (or "an"), "one or more" and "at least one" can be used interchangeably herein.

Where a range of values is provided, it is understood that each intervening value, and any combination or subcombination of intervening values, between the upper and lower limit of that range and any other stated or intervening value in that stated range, is encompassed within the range of values recited.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number, and thus will typically refer to a number or value that is 10% below or above the specifically recited number or value.

The disclosed methods may be utilized to treat and/or prevent secondary hyperthyroidism in a patient in need thereof. A patient in need thereof may include, but is not limited to, a patient having or at risk for developing secondary hyperthyroidism subsequent to a renal disease or disorder. A patient in need thereof may include, but is not limited to, a patient having or at risk for developing secondary hyperthyroidism subsequent to renal osteodystrophy, for example, due to renal failure. A patient in need thereof may include a patient undergoing renal dialysis. A patient in need thereof may include, but is not limited to, a patient having or at risk for developing secondary hyperthyroidism as a result of a gastrointestinal malabsorption syndromes (e.g., chronic pancreatitis small bowel disease, and malabsorption-dependent bariatric surgery in which the intestines do not absorb vitamins and minerals properly). A patient in need thereof may include, but is not limited to, a patient having or at risk for developing secondary hyperthyroidism as a result of a long-term lithium therapy, vitamin D deficiency, malnutrition, vitamin D-resistant rickets, or hypermagnesemia (i.e., abnormally high blood magnesium levels).

The disclosed methods may be utilized to treat and/or prevent the symptoms of secondary hyperthyroidism in a patient in need thereof. Symptoms of secondary hyperthyroidism treated and/or prevented by the disclosed methods may include, but are not limited to: weakening of the bones; calciphylaxis (when calcium forms clumps in the skin and lead to ulcers and potentially death of surrounding tissue); cardiovascular complications; abnormal fat and sugar metabolism; itching (pruritis); and low blood counts (anemia). Other symptoms of secondary hyperthyroidism treated and/or prevented by the disclosed methods may include: increased levels of serum PTH, serum phosphorus, and serum creatinine. Further symptoms of secondary hyperthyroidism treated and/or prevented by the disclosed methods may include: bone and joint pain, bone deformities, broken bones (fractures), swollen joints, kidney stones, increased urination, muscle weakness and pain, nausea, and loss of appetite. Even further symptoms of secondary hyperthyroidism treated and/or prevented by the disclosed methods may include: fatigue, upper abdominal pain, and depression.

Previously, it has been demonstrated that 300 ng per day of $1\alpha,25$-dihydroxyvitamin $D_3$ ($1,25(OH)_2D_3$) administered through the diet can effectively pre em renal disease and renal failure by reducing the symptoms of renal disease. (See James Wonkee Kim. Effects of $1\alpha,25$-dihydroxyvitamin $D_3$ on the MRL/MpJ-fas/lpr model of systemic lupus erythematosus (Ph. D. Thesis, University of Wisconsin-Madison (2009)). For instance, it has been previously shown that administering $1\alpha,25$-dihydroxyvitamin $D_3$ ($1,25(OH)_2D_3$) completely prevents proteinuria in the MRL/MpJ-FAS$^{lpr}$ (MRL/lpr) mouse model of systemic lupus erythematosus (SLE). (See id.). However, severe hypercalcemia always accompanied this treatment. Hypercalcemia (i.e., increased levels of calcium in the blood) can result in serious physical problems, including death. Specifically, an increase in calcium of approximately 2 mg/100 ml is considered mild hypercalcemia and is not considered a problem. However, an increase in calcium levels of more than 2 mg/100 ml is considered severe hypercalcemia and can cause calcification of the kidney, heart, and aorta. Clearly, the use of this compound is not optimal to treat or prevent secondary hyperparathyroidism, or the symptoms thereof, because of the resultant hypercalcemia.

2-methylene-19-nor-(20S)-$1\alpha,25$-dihydroxyvitamin $D_3$ (2MD) is an analog of $1,25(OH)_2D_3$ which has been shown to have increased in vivo potency toward bone but not on intestinal calcium absorption. The overall synthesis of 2MD is illustrated and described more completely in U.S. Pat. No. 5,843,928, issued Dec. 1, 1998, and entitled "2-Alkylidene-19-Nor-Vitamin D Compounds" the specification of which is specifically incorporated herein by reference. The biological activity of 2MD is also reported in U.S. Pat. No. 5,843,928 and in Shevde et al., "A Potent Analog of $1\alpha,25$-dihydroxyvitamin $D_3$ Selectively Induces Bone Formation" PNAS, Vol. 99, No. 21 pp 13487-13491 (2002), both of which are specifically incorporated herein by reference.

In the methods disclosed herein, 2MD can be administered to treat and/or prevent secondary hyperparathyroidism and/or its accompanying symptoms without causing severe hypercalcemia, while also resulting in reduced levels of phosphorus and creatinine in blood as well as decreased PTH levels in the blood.

Also in the methods disclosed herein, 2MD can be used to treat and reduce the severity of secondary hyperparathyroidism of renal disease and its accompanying symptoms, without causing severe hypercalcemia, by reducing phosphorus, creatinine and PTH levels in blood.

As used herein, "hypercalcemia" means elevated calcium levels in the blood of more than 2 mg/100 ml. In a normal subject, calcium levels are approximately 9-10.5 mg/dL or 2.2-2.6 mmol/L. In cases of severe hypercalcemia (i.e., calcium levels above 15-16 mg/dL or 3.75-4 mmol/L) coma and cardiac arrest can develop.

The present invention therefore provides novel methods of treating and/or preventing secondary hyperparathyroidism and/or its accompanying symptoms in a subject at risk of developing secondary hyperparathyroidism, and of treating and/or preventing secondary hyperparathyroidism and/or its accompanying symptoms in a subject exhibiting symptoms of secondary hyperparathyroidism, by administering to the subject a therapeutically effective amount of 2-methylene-19-nor-(20S)-1α,25-dihydroxyvitamin D$_3$ (2MD) or pharmaceutically acceptable salts thereof without inducing hypercalcemia in the subject, where 2MD has the structure (I):

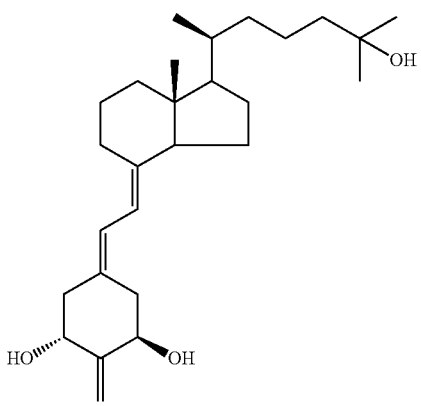

As used herein, "preventing" means forestalling of a clinical symptom indicative of secondary hyperparathyroidism. Such forestalling includes, for example, the maintenance of normal kidney functions in a subject at risk of developing secondary hyperparathyroidism prior to the development of overt symptoms of secondary hyperparathyroidism including, but not limited to, increased levels of serum PTH, phosphorus and creatinine. Therefore, the term "preventing" includes the prophylactic treatment of subjects to guard them from the occurrence of secondary hyperparathyroidism. Preventing secondary hyperparathyroidism in a subject is also intended to include inhibiting or arresting the development of secondary hyperparathyroidism. Inhibiting or arresting the development of secondary hyperparathyroidism includes, for example, inhibiting or arresting the occurrence of increased levels of serum PTH, phosphorus and creatinine.

As used herein, a "renal disease" or a "renal disorder" means a condition exhibiting impaired kidney function in a subject who is not on dialysis or a patient with chronic kidney disease (CKD) at stages 2 or 3, such as, for instance, acute kidney failure, acute nephritic syndrome, analgesic nephropathy, atheroembloic renal disease, chronic kidney failure, chronic nephritis, congenital nephrotic syndrome, goodpasture syndrome, interstitial nephritis, kidney cancer, kidney damage, kidney infection, kidney injury, kidney stones, membranoproliferative GNI, membranoproliferative GNII, membranous nephropathy, minimal change disease, necrotizing glomerulonephritis, nephroblastoma, nephrocalcinosis, nephrogenic diabetes insipidus, nephropathy-IgA, nephrosis nephrotic syndrome, polycystic kidney disease, post-strepococcal GN, reflux nephropathy, renal artery embolism, renal artery stenosis, renal disorders, renal papillary necrosis, renal tubular acidosis type I, renal tubular acidosis type II, renal underperfusion, renal vein thrombosis. "Renal disease" is also meant to include patients with established kidney failure (e.g., a glomerular filtration rate (GFR) of less than 15 mL/min/1.73 m$^2$ or permanent renal replacement therapy (RRT)). A subject having "renal disease" is meant to include a subject who has had kidney damage for more than 3 months, as defined by structural or functional abnormalities of the kidney, with or without decreased GFR, manifested by either pathological abnormalities or markers of kidney damage, including abnormalities in the composition of the blood or urine, or abnormalities in imaging tests. Markers of kidney damage include proteinuria of greater than 300 μg/day as measured by 24-HR excretion method. (See Table 15, Am. J. of Kidney Diseases, v. 39, no. 2, Suppl. 1 (February 2002), pp. 546-575 incorporated herein by reference). This definition may include patients on dialysis.

As used herein, a patient having "stage 2 chronic kidney disease (CKD)" means a patient exhibiting a mild reduction in GFR (60-89 mL/min/1.73 m$^2$). Kidney damage is defined as pathologic abnormalities or markers of damage, including abnormalities in blood or urine test or imaging studies. A patient having "stage 3 chronic kidney disease (CKD)" means a patient exhibiting a moderate reduction in GFR (30-59 mL/min/1.73 m$^2$). Guidelines for characterizing kidney disease may distinguish between stage 3A (GFR 45-59) and stage 3B (GFR 30-44) for purposes of screening and referral. For more information about stages of kidney disease, see Am. J. of Kidney Disease, V. 39, No. 2, Suppl. 1, February 2002 incorporated herein by reference.

As used herein, a "subject" includes mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. The primary subjects to which the present invention is directed are the class of humans being treated with, or receiving, hemodialysis. The term "subject" may be utilized herein interchangeably with the terms "patient" or "individual."

As used herein, "administering" mean introducing a compound into the body, preferably into the systemic circulation, as described in more detail below. Examples include but are not limited to oral, topical, buccal, sublingual, pulmonary, transdermal, transmucosal, as well as subcutaneous, intraperitoneal, intravenous, and intramuscular injection or in the form of liquid or solid doses is the alimentary canal.

Figure 13:
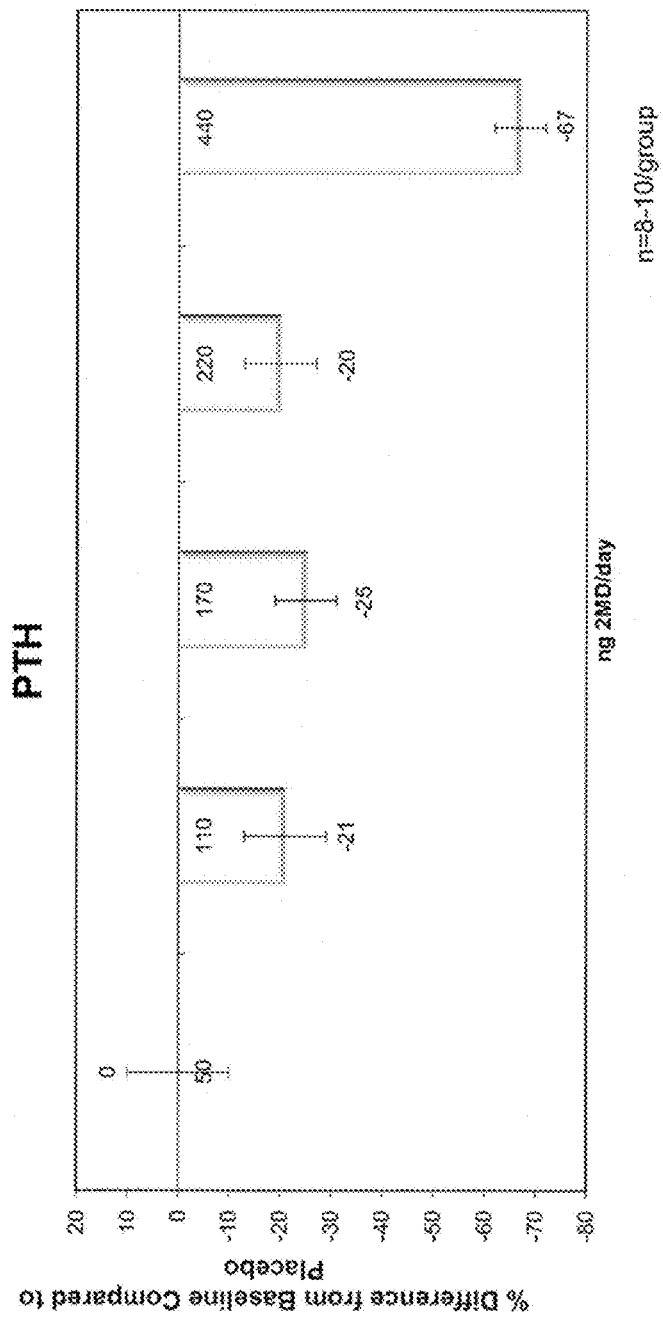
FIG. 13 is a graph illustrating the effect of oral administration of 2MD at various doses on serum PTH in a Phase 1B human trial of postmenopausal women.

As used herein, "therapeutically effect" means an amount of a compound that, when administered to a subject for treating or preventing a disease, is sufficient to effect such treatment of prevention of the disease. A "therapeutically effective amount" will vary depending on the compound, the disease state being, treated, the severity or the disease treated, the age and relative health of the subject, the route and form of administration, the judgment of the attending medical or veterinary practitioner, and other factors. As disclosed herein, male weanling Harlan-Sprague Dawley rats were administered several dose levels of 2MD that would not cause significant hypercalcemia. We found that 2½ nanograms/kilogram body weight (ng/kg bw) of 2MD per rat per day is sufficient to prevent and treat secondary hyperparathyroidism, or to prevent or treat symptoms of secondary hyperparathyroidism, without increasing serum calcium levels. Furthermore, 400 ng per day of 2MD in postmenopausal women showed over a 60% reduction in serum PTH levels while maintaining serum calcium levels within the physiologically normal range (FIG. 13).

In one embodiment, the therapeutically effective amount ranges from between about 10 ng/day to about 1 µg/day, and preferably from between about 20 ng/day to about 1 µg/day. In a more preferred embodiment, the therapeutically effective amount ranges from between about 40 ng/day to about 600 ng/day, or between about 50 ng/day to about 600 ng/day. In the most preferred embodiment, the therapeutically effective amount ranges from between about 100 ng/day to about 400 ng/day.

As used herein, "treat," "treating" or "treatment" means amelioration, alleviation or abation of a clinical symptom indicative of secondary hyperparathyroidism. Amelioration, alleviation or abation of a clinical symptom includes, for example, arresting, reducing the severity of or slowing the progression of or causing the regression of a symptom of secondary hyperparathyroidism. For instance, lowering the amount of serum PTH, serum phosphorus or serum creatinine levels in response to treatment with 2MD. Specifically, treating may include reducing the amount of serum PTH, serum phosphorus or serum creatinine by at least about 20%. In one embodiment, the amount of serum PTH serum phosphorus or serum creatinine in the subject's blood is reduced by about 20-40% or about 35-50%. Other pathological conditions, chronic complications or phenotypic manifestations of secondary hyperparathyroidism are known to those skilled in the art and can similarly be used as a measure of treating secondary hyperparathyroidism so long as there is a reduction in the severity of the condition, complication or manifestation associated with the disease.

Effective compound formulations are described in U.S. Pat. No. 5,843,928 and include pharmaceutical applications as a solution in innocuous solvents, or as an emulsion, suspension or dispersion in suitable solvents or carriers, or as pills, tablets, capsules combined with solid carriers. Other formulations ma also include other pharmaceutically acceptable and nontoxic excipients such as stabilizers, anti-oxidants, binders, coloring agents or emulsifying or taste-modifying agents and extended release formulations.

In one embodiment, the 2MD compound is the active pharmaceutical ingredient (API) administered in the disclosed methods. The API may be formulated in an oral pharmaceutical dosage form as a solution in innocuous solvents, emulsion, suspension or dispersion in suitable solvents or carriers. The API may also be formulated in various oral dosage forms, such as pills, tablets or capsules using suitable pharmaceutical solid carriers. Such pharmaceutical formulations may also contain other pharmaceutically suitable USP-approved inactive ingredients, excipients, such as stabilizers, anti-oxidants, binders, coloring agents, emulsifiers, and/or taste-modifying, agents, which are referred to as USP approved inactive pharmaceutical ingredients.

The API may be administered orally, topically, parenterally or transdermally or by inhalation. The compound may be administered by injection or intravenous infusion using suitable sterile solutions. Topical dosage forms may be creams, ointments, patches, or similar vehicles suitable for transdermal and topical dosage forms.

In some embodiments, the API may be formulated in doses for delivering a dose ranging from between about 10 ng/day to about 1 µg/day, preferable from between about 20 ng/day to about 1 µg/day, and more preferably from between about 40 ng/day to about 600 ng/day, or from between about 50 ng to about 600 ng per day and most preferably from between about 100 ng/day to about 400 ng/day. The API preferably is formulated in a dose that may be used for the prevention or treatment of secondary hyperparathyroidism, or for the prevention or treatment of symptoms of secondary hyperparathyroidism. Typically, the positive effects of 2MD are observed at dose levels that do not significantly raise serum calcium. Such dose and dosing regimens may be adjusted to accommodate disease severity or progression, patient predisposition/at-risk/susceptible-to and other known criteria.

The pharmaceutically suitable oral carrier systems (also referred to as drug delivery systems, which are modern technology, distributed with or as a part of a drug product that allows for the uniform release or targeting or drugs to the body) preferably include FDA-approved and/or USP-approved inactive ingredients. Under 21 CFR 210.3(b)(8), an inactive ingredient is any component of a drug product intended to furnish pharmaceutical activity or other direct effect in the diagnosis, or to affect the structure or any function of the body of humans or other animal. Active ingredients include those components of the product that may undergo chemical change during the manufacture of the drug product and be present in the drug product in a modified form intended to furnish the specified activity or effect. As use herein, a kit (also referred to as a dosage form) is a packaged collection of related material.

As used herein, "oral dosage" forms may include capsules (i.e., a solid oral dosage form consisting of a shell and a filling), whereby the shell is composed of a single sealed enclosure, or two halves that fit together and which are sometimes sealed with a band, and whereby capsule shells may be made from gelatin, starch, or cellulose, or other suitable materials, may be soft or hard, and are filled with a solid or liquid ingredients that can be poured or squeezed. The oral dosage form may also be a capsule or coated pellets, in which the drug is enclosed within either a hard or soft soluble container or "shell" made from a suitable form of gelatin. The drug itself may be in the form of granules to which varying amount of coating have been applied, or in a capsule coated extended release, in which the drug is enclosed within either a hard or soft soluble container or "shell" made from a suitable term of gelatin. Additionally, the capsule may be covered in a designated coating which releases a drug or drugs in such a manner to allow at least a reduction in dosing frequency as compared to that drug or drugs presented as a conventional dosage form.

The oral dosage form may further be a capsule delayed release, in which the drug is enclosed within either a hard or soft soluble continuer made from a suitable form of gelatin, and which releases a drug (or drugs) at a time other than promptly after administration, whereby enteric-coated articles are delayed release dosage forms. Capsule delayed release pellets, in which the drug is enclosed within either a hard or soft container or "shell" are also useful. In these cases, the drug itself is in the form of granules to which enteric coating has been applied, thus delaying release of the drug until its passing into the intestine. Capsule extended release and capsule film-coated extended release are also useful.

Additionally, the capsule is covered in a designated film coating, and which releases a drug or drugs in such a manner to allow at least a reduction in dosing frequency as compared to that drug or drugs presented as a conventional dosage form), capsule gelatin coated (a solid dosage form in which the drug is enclosed within either a hard or soft soluble container made from a suitable form of gelatin; through a banding process, the capsule is coated with additional layers of gelatin so as to form a complete seal), capsule liquid filled (a solid dosage form in which the drug is enclosed within a soluble, gelatin shell which is plasticized by the addition of a polyol, such as sorbitol or glycerin, and is therefore of a somewhat thicker consistency than that of a hard shell capsule).

Typically, the active ingredients may be dissolved or suspended in a liquid vehicle, a granule (a small particle or grain), a pellet (a small sterile solid mass consisting of a highly purified drug, with or without excipients, made by the formation of granules, or by compression and molding), or a pellet coated extended release (a solid dosage form in which the drug itself is in the form of granules to which varying amounts of coating have been applied, and which releases a drug or drugs in such a manner to allow a reduction in dosing frequency as compared to that drug or drugs presented as a conventional dosage form).

Other forms include pills (a small, round solid dosage form containing a medicinal agent intended for oral administration), powder (an intimate mixture of dry, finely divided drugs and/or chemicals that may be intended for internal or external use), elixir (a clear, pleasantly flavored, sweetened hydroalcoholic liquid containing dissolved medicinal agents; it is intended for oral use), chewing gum (a sweetened and flavored insoluble plastic material of various shapes which when chewed, releases a drug substance into the oral cavity), syrup (an oral solution containing high concentrations of sucrose or other sugars; the term has also been used to include any other liquid dosage form prepared in a sweet and viscid vehicle, including oral suspensions), tablet (a solid dosage form containing medicinal substances with or without suitable diluents), tablet chewable (a solid dosage form containing medicinal substances with or without suitable diluents that is intended to be chewed, producing a pleasant tasting residue in the oral cavity that is easily swallowed and does not leave a bitter or unpleasant aftertaste), tablet coated or tablet delayed release, tablet dispersible, tablet effervescent, tablet extended release, tablet film coated, or tablet film coated extended release where the tablet is formulated in such manner as to make the contained medicament available over an extended period of time following ingestion.

In other forms, a tablet for solution, tablet for suspension, tablet multilayer, tablet multilayer extended release may be provided, where the tablet is formulated in such manner as to allow at least a reduction in dosing frequency as compared to that drug presented as a conventional dosage form. A tablet orally disintegrating, tablet orally disintegrating delayed release, tablet soluble, tablet sugar coated, osmotic, and the like are also suitable.

The oral dosage form composition may contain an active pharmaceutical ingredient and one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (e.g., anionic, cationic, amphoteric and nonionic), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

As used herein, the injectable and infusion dosage forms include, but are not limited to, a liposomal injectable, which either consists of or forms liposomes (a lipid bilayer vesicle usually composed of phospholipids which is used to encapsulate an active drug substance). An injection, which includes a sterile preparation intended for parenteral use five distinct classes of injections exist as defined by the USP, is also suitable. An emulsion injection, which includes an emulsion consisting of a sterile, pyrogen-free preparation intended to be administered parenterally or a lipid complex injection are also suitable.

Other forms include a powder for solution injection, which is a sterile preparation intended for reconstitution to form a solution for parenteral use; a powder for suspension injection that is a sterile preparation intended for reconstitution to form a suspension for parenteral use; a powder lyophilized for liposomal suspension injection, which is a sterile freeze dried preparation intended for reconstitution for parenteral use which has been formulated in a manner that would allow liposomes (a lipid bilayer vesicle usually composed of phospholipids which is used to encapsulate an active drug substance, either within a lipid bilayer or in an aqueous space) to be formed upon reconstitution; a powder lyophilized for solution injection, which is a dosage form intended for the solution prepared by lyophilization ("freeze drying"), a process which involves the removal of water from products in the frozen state at extremely low pressures.

This is intended for subsequent addition of liquid to create a solution that conforms in all respects to the requirements for injections; a powder lyophilized for suspension injection being a liquid preparation, intended for parenteral use that contains solids suspended in a suitable fluid medium and conforms in all respects to the requirements for Sterile Suspensions; the medicinal agents intended for the suspension are prepared by lyophilization ("freeze drying"), a process which involves the removal of water from products in the frozen state at extremely low pressures; a solution injection being a liquid preparation containing one or more drug substances dissolved in a suitable solvent or mixture of mutually miscible solvents that is suitable for injection; a solution concentrate injection being a sterile preparation for parenteral use which, upon the addition of suitable solvents, yields a solution conforming in all respects to the requirements for injections.

A suspension injection comprises a liquid preparation, suitable for injection, which consists of solid particles dispersed throughout a liquid phase in which the particles are not soluble that can also consist of an oil phase dispersed throughout an aqueous phase, or vice-versa. A suspension liposomal injection comprises a liquid preparation, suitable for injection, which consists of an oil phase dispersed throughout an aqueous phase in such a manner that liposomes (a lipid bilayer vesicle usually composed of phospholipids which is used to encapsulate an active drug substance, either within a lipid bilayer or in an aqueous space) are formed. A suspension sonicated injection comprises a liquid preparation, suitable for injection, which consists of solid particles dispersed throughout a liquid, phase in which the particles are not soluble. In addition, the product is sonicated while a gas is bubbled through the suspension, and this results in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives. Formulations suitable for parenteral administration conveniently comprise a sterile oily or aqueous preparation of the active ingredient which is preferably isotonic with the blood of the recipient.

As used herein, inhalation dosage forms include, but are not limited to, aerosol being a product that is packaged under pressure and contains therapeutically active ingredients that are released upon activation of an appropriate valve system intended for topical application to the skin as well as local application into the nose (nasal aerosols), mouth (lingual and sublingual aerosols), or lungs (inhalation aerosols); foam aerosol being a dosage form containing one or more active ingredients, surfactants, aqueous or nonaqueous liquids, and the propellants, whereby if the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged; metered aerosol being, a pressurized dosage form consisting of metered dose valves which allow for the delivery of a uniform quantity of spray upon each activation; powder aerosol being a product that is packaged under pressure and contains therapeutically active ingredients, in the form of a powder, that are released upon activation of an appropriate valve system; and, aerosol spray being an aerosol product which utilizes a compressed gas as the propellant to provide the force necessary to expel the product as a wet spray and being applicable to solutions of medicinal agents in aqueous solvents.

As used herein, transdermal dosage form includes, but is not limited to, a patch being a drug delivery system that often contains an adhesive backing that is usually applied to an external site on the body, whereby the ingredients either passively diffuse from, or are actively transported from, some portion of the patch, and whereby depending upon the patch, the ingredients are either delivered to the outer surface of the body or into the body; and, other various types of transdermal patches such as matrix, reservoir and others known in the art.

As used herein, the topical dosage form includes various dosage forms known in the art such as lotions (an emulsion, liquid dosage form, whereby this dosage form is generally for external application to the skin), lotion augmented (a lotion dosage form that enhances drug delivery, whereby augmentation does not refer to the strength of the drug in the dosage form), gels (a semisolid dosage form that contains a gelling agent to provide stiffness to a solution or a colloidal dispersion, whereby the gel may contain suspended particles) and ointments (a semisolid dosage form, usually containing less than 20% water and volatiles and greater than 50% hydrocarbons, waxes, or polyols as the vehicle, whereby this dosage form is generally for external application to the skin or mucous membranes).

Ointment augmented (an ointment dosage form that enhances drug delivery, whereby augmentation does not refer to the strength of the drug in the dosage form), creams (an emulsion, semisolid dosage form, usually containing greater than 20% water and volatiles and/or less than 50% hydrocarbons, waxes, or polyols may also be used as the vehicle, whereby this dosage form is generally for external application to the skin or mucous membranes. Cream augmented (a cream dosage form that enhances drug delivery, whereby augmentation does not refer to the strength of the drug in the dosage form), emulsions (a dosage form consisting of a two-phase system comprised of at least two immiscible liquids, one of which is dispersed as droplets, internal or dispersed phase, within the other liquid, external or continuous phase, generally stabilized with one or more emulsifying agents, whereby emulsion is used as a dosage form term unless a more specific term is applicable, e.g. cream, lotion, ointment), suspensions (a liquid dosage form that contains solid particles dispersed in a liquid vehicle), suspension extended release, pastes (a semisolid dosage form, containing a large proportion, 20-50%, of solids finely dispersed in a fatty vehicle, whereby this dosage form is generally for external application to the skin or mucous membranes), solutions a clear, homogeneous liquid dosage form that contains one or more chemical substances dissolved in a solvent or mixture of mutually miscible solvents), and powders are also suitable.

Shampoos (a lotion dosage form which has a soap or detergent that is usually used to clean the hair and scalp) are often used as a vehicle for dermatologic agents. For instance, shampoo suspensions (a liquid soap or detergent containing, one or more solid, insoluble substances dispersed in a liquid vehicle that is used to clean the hair and scalp and is often used as a vehicle for dermatologic agents) are often used. Aerosol foams (i.e., a dosage form containing one or more active ingredients, surfactants, aqueous or nonaqueous liquids, and the propellants; if the propellant is in the internal discontinuous phase, i.e., of the oil-in-water type, a stable foam is discharged, and if the propellant is in the external continuous phase, i.e., of the water-in-oil type, a spray or a quick-breaking foam is discharged), sprays (a liquid minutely divided as by a jet of air or steam), metered spray (a non-pressurized dosage form consisting of valves which allow the dispensing of a specified quantity of spray upon each activation), and suspension spray (a liquid preparation containing solid particles dispersed in a liquid vehicle and in the form of coarse droplets or as finely divided solids to be applied locally, most usually to the nasal-pharyngeal tract, or topically to the skin) are also suitable.

Jellies (a class of gels, which are semisolid systems that consist of suspensions made up of either small inorganic particles or large organic molecules interpenetrated by a liquid—in which the structural coherent matrix contains a high portion of liquid, usually water) and films (a thin layer or coating), including film extended release (a drug delivery system in the form of a film that releases the drug over an extended period in such a way as to maintain constant drug levels in the blood or target tissue) and film soluble (a thin layer or coating which is susceptible to being dissolved when in contact with a liquid) are also suitable.

Sponges (a porous, interlacing, absorbent material that contains a drug, whereby it is typically used for applying or introducing medication, or for cleansing and whereby a sponge usually retains its shape), swabs (a small piece of relatively flat absorbent material that contains a drug, whereby a swab may also be attached to one end of a small stick, and whereby a swab is typically used for applying, medication or for cleansing).

Patches (a drug delivery system that often contains an adhesive backing that is usually applied to an external site on the body, whereby its ingredients either passively diffuse from, or are actively transported from, some portion of the patch, whereby depending upon the patch, the ingredients are either delivered to the outer surface of the body or into the body, and whereby a patch is sometimes synonymous with the terms 'extended release film' and 'system'), patch extended release (a drug delivery system in the form of a patch that releases the drug in such a manner that a reduction in dosing frequency compared to that drug presented as a conventional dosage form, e.g., a solution or a prompt drug-releasing, conventional solid dosage form), patch extended release electronically controlled (a drug delivery system in the form of a patch which is controlled by an electric current that releases the drug in such a manner that a reduction in dosing frequency compared to that drug presented as a conventional dosage form, e.g., a solution or a prompt drug-releasing, conventional solid dosage form), and the like. The various topical dosage forms may also be formulated as immediate release, controlled release, sustained release, or the like.

The topical dosage form composition contains an active pharmaceutical ingredient and one or more inactive pharmaceutical ingredients such as excipients, colorants, pigments, additives, fillers, emollients, surfactants (e.g., anionic, cationic, amphoteric and nonionic), penetration enhancers (e.g., alcohols, fatty alcohols, fifty acids, fatty acid esters and polyols), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

EXAMPLES

The following examples are presented for illustrative purposes only, and are not intended to limit the scope of the present invention in any way. The examples illustrate that 2MD, an analog of $1,25(OH)_2D_3$ originally thought to be important in prevention and treatment of osteoporosis, is also important in preventing and treating secondary hyperparathyroidism and its accompanying symptoms. A study conducted in rats in which their kidneys were surgically removed, showed that daily oral and intraperitoneal (ip) 2MD administration results in lower levels of serum PTH, phosphorus, and creatinine, all indicators of kidney failure, as compared to vehicle control animals. Furthermore, 2MD administration results in lower PTH, phosphorus and creatinine levels at dose levels that do not raise serum calcium.

Example 1

Materials and Methods

Nephrectomy Rat Model. Disease Induction. Weanling, male Sprague-Dawley rats were obtained from Harlan (Madison, Wis.). Following a 10-13 day acclimation period, the animals had two-thirds of one kidney removed. After a week, the other entire kidney was removed. The animals were then switched from a chow diet to a purified rodent diet (Suda et al., Purified Rodent Diet-Diet 11) containing 0.6% Ca and 0.9% phosphorus and fat soluble vitamins A, D, E and K. Water and diet were provided ad libitum.

Animal Husbandry. Animals were housed in suspended, plastic shoe-box style cages with corn cob bedding (prior to surgery) or in stainless steel, wire-bottom cages (approximately one week after surgery). The animal rooms were maintained at a temperature of 68 to 72° F. and a relative humidity of 25 to 75%. The holding rooms were set to provide 12 hours of light per day.

Treatment Groups. Approximately four weeks after the second surgery, animals were assigned to treatment groups (14-15 animals/group) so that each group had the same average PTH level.

Dose Preparation (Vehicle Formulation). The negative control material was prepared by volumetrically measuring ethanol (5%) and Nether oil, mixing and then placing in storage at 2 to 8° C.

Dose Preparation (2MD Formulation). 2MD formulations (DP001, Sigma Aldrich Fine Chemicals. Madison, Wis.) were prepared by first determining the concentration of an ethanol stock solution using UV spectrophotometry (extinction coefficient=42,000; $\lambda_{max}$=252 nm). The solutions were then volumetrically added to Neobee oil so that there was no more than 5% ethanol in the final solution. If necessary, additional ethanol was added to bring the final ethanol amount to 5%. The solution was mixed and stored at 2 to 8° C.

Dose Administration Method. Both vehicle and 2MD were administered orally to the back of the tongue at 0.5 ml/kg body weight once daily for 8 weeks, or intraperitoneally three times per week for 4 weeks.

Serum Parathyroid Hormone (PTH) Levels. By "serum PTH levels" we mean the amount of PTH released by the parathyroid gland. PTH is the most important regulator of the body's calcium and phosphorus levels, and is controlled by the level of calcium in the blood. Low blood calcium levels cause increased PTH to be released, while high blood calcium levels inhibit PTH release. Normal values are 10-55 picograms per milliliter (pg/mL). Four weeks after surgery and 4 and 8 weeks after treatment initiation, blood was collected from the tail artery and the concentration of bioactive serum PTH was measured using the rat BioActive Intact PTH ELISA Kit from Immutopics, Inc. (San Clemente, Calif.).

Serum Calcium Analysis. Four weeks following surgery and 4 and 8 weeks after treatment started, blood was collected from the tail artery of each experimental animal. The blood was allowed to coagulate at room temperature and then centrifuged at 3000×g for 15 minutes. The serum was transferred to a polypropylene tube and stored frozen at −20° C. The level of calcium was determined by diluting the serum into 0.1% lanthum chloride and measuring the absorbance on an atomic absorption spectrophotometer (Perkin Elmer Model 3110, Shelton, Conn.).

Phosphorus Assay. Four weeks after surgery and 8 weeks after treatment started, blood was collected from the tail artery of each experimental animal. The blood was allowed to coagulate at room temperature and then centrifuged at 3000×g for 15 minutes. The serum was transferred to a polypropylene tube and stored frozen at −20° C. The level of phosphorus was determined using a clinical analyzer (Pentra 400, Horiba ABX Diagnostics—France; UV method using phosphomolybdate).

Creatinine Assay. Measuring serum creatinine levels is a useful and inexpensive method of evaluating renal dysfunction. Creatinine is a non-protein waste product of phosphocreatinine metabolism by skeletal muscle tissue. Creatinine production is continuous and is proportional to muscle mass. Creatinine is freely filtered and therefore the serum creatinine level depends on the Glomerular Filtration Rate (GFR). Renal dysfunction diminishes the ability to filter creatinine and the serum creatinine rises. If the serum creatinine level doubles, the GFR is considered to have been halved. A threefold increase is considered to reflect a 75% loss of kidney function.

In the following examples, serum creatinine levels were evaluated four weeks after surgery and 8 weeks after treatment started. Blood was collected from the tail artery of each experimental animal. The blood was allowed to coagulate at room temperature and then centrifuged at 3000×g for 15 minutes. The serum was transferred to a polypropylene tube and stored frozen at −20° C. The level of creatinine was determined using a clinical analyzer (Pentra 400, Horiba ABX Diagnostics—France; Jaffe reaction) and is indicative of impaired renal function and chronic nephritis. In one embodiment of the invention, a minimum decrease in serum creatinine levels of approximately 30% is expected after treatment according to the method of the present invention.

Example 2

Uremic Rat Model—Intraperitoneal (ip) Administration of 2MD

Figure 2:
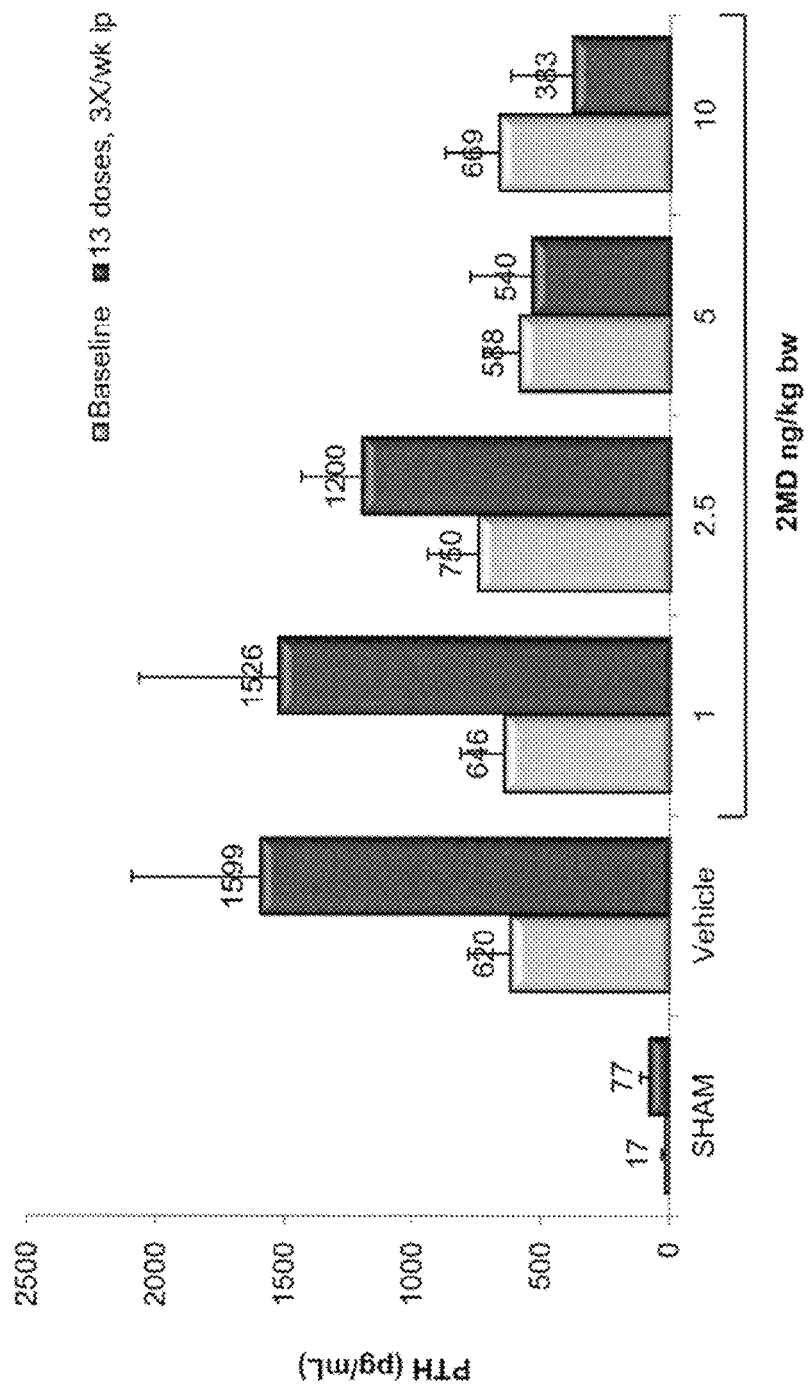
FIG. 2 is a graph illustrating the effect of intraperitoneal administration of 2MD at various doses on serum PTH in a uremic rat model.
Figure 3:
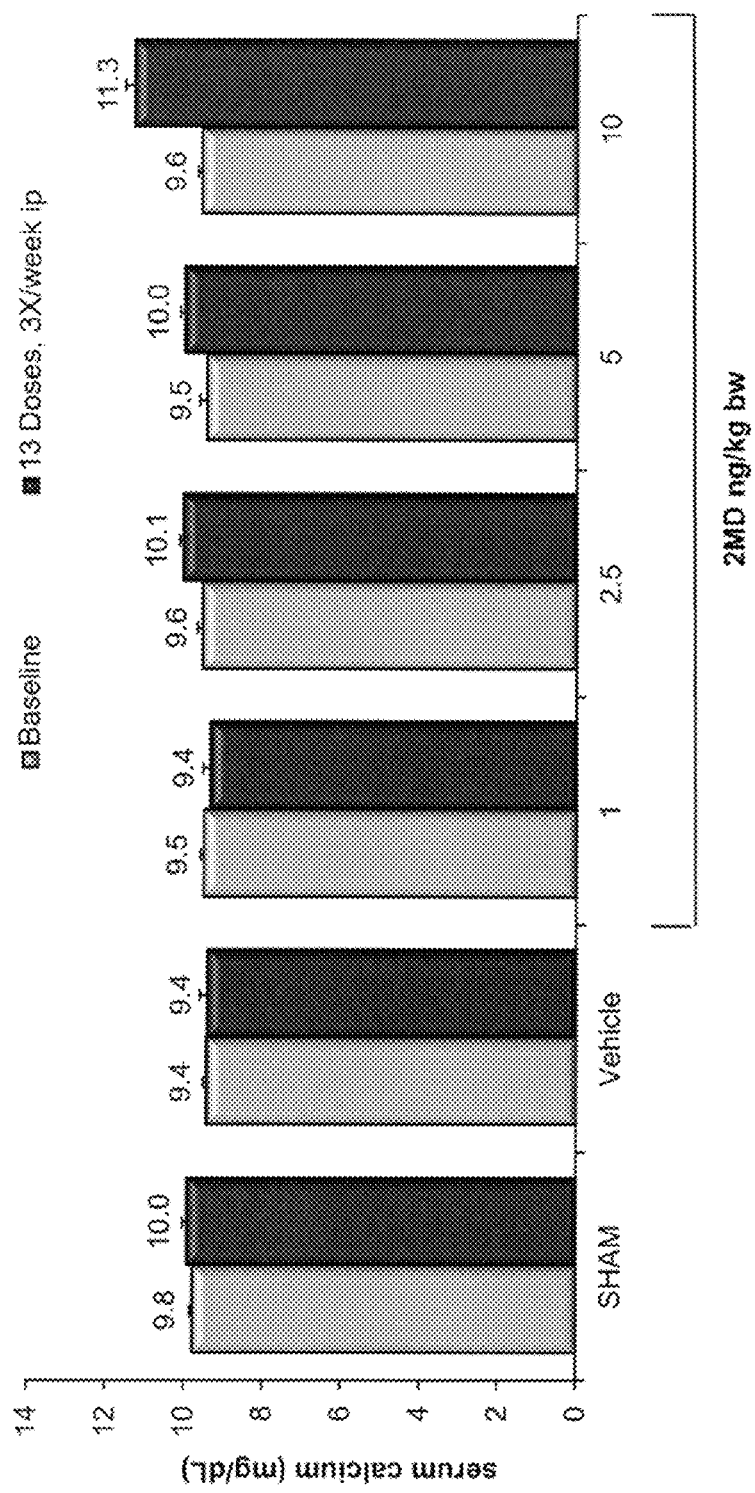
FIG. 3 is a graph illustrating the effect of intraperitoneal administration of 2MD at various doses on serum calcium in a uremic rat model.

FIG. 1 schematically illustrates the ip treatment protocol with 2MD. As shown in FIG. 2, ip administration of 2M D at 5 ng/kg bw three times per week prevented increases in serum PTH, and suppresses circulating PTH levels at 10 ng/kg bw. As shown in FIG. 3, ip administration of 2MD did not raise serum calcium levels until a dose of 10 ng/kg bw was administered.

Example 3

Lifeline Rat Model Oral Administration of 2MD compared to Zemplar®

Figure 4:
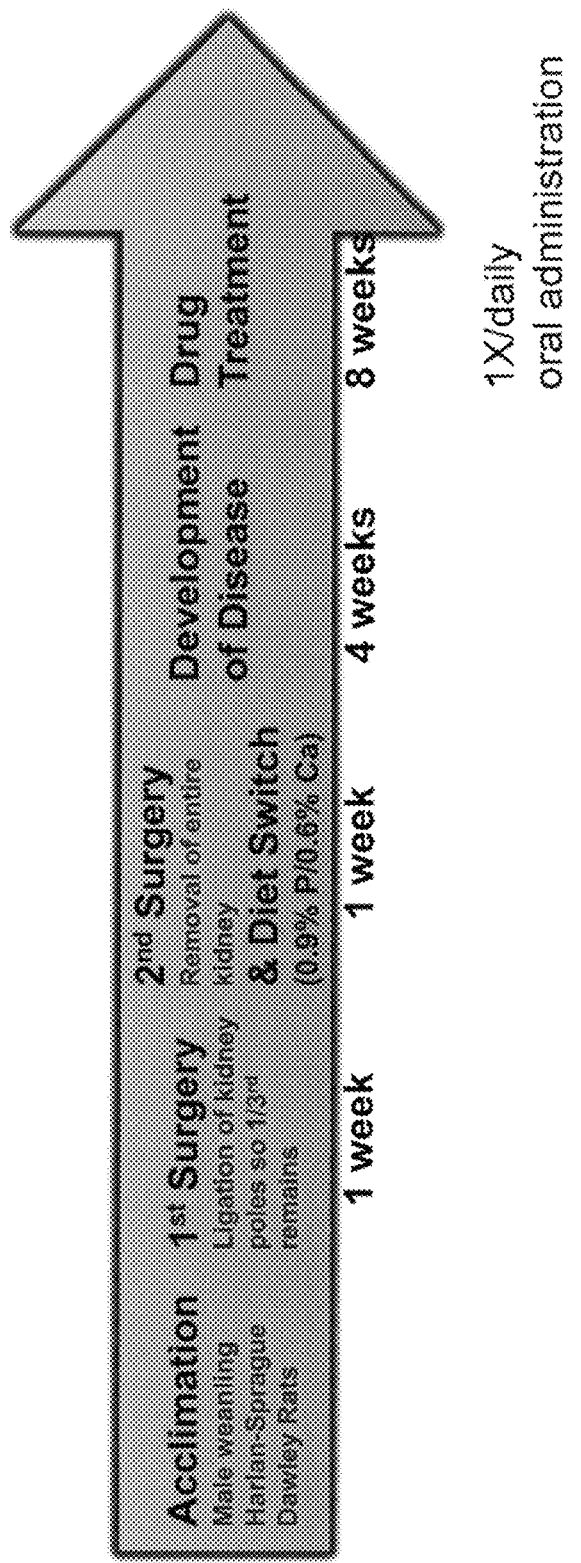
FIG. 4 schematically illustrates the oral treatment protocol with 2MD contemplated herein.
Figure 5:
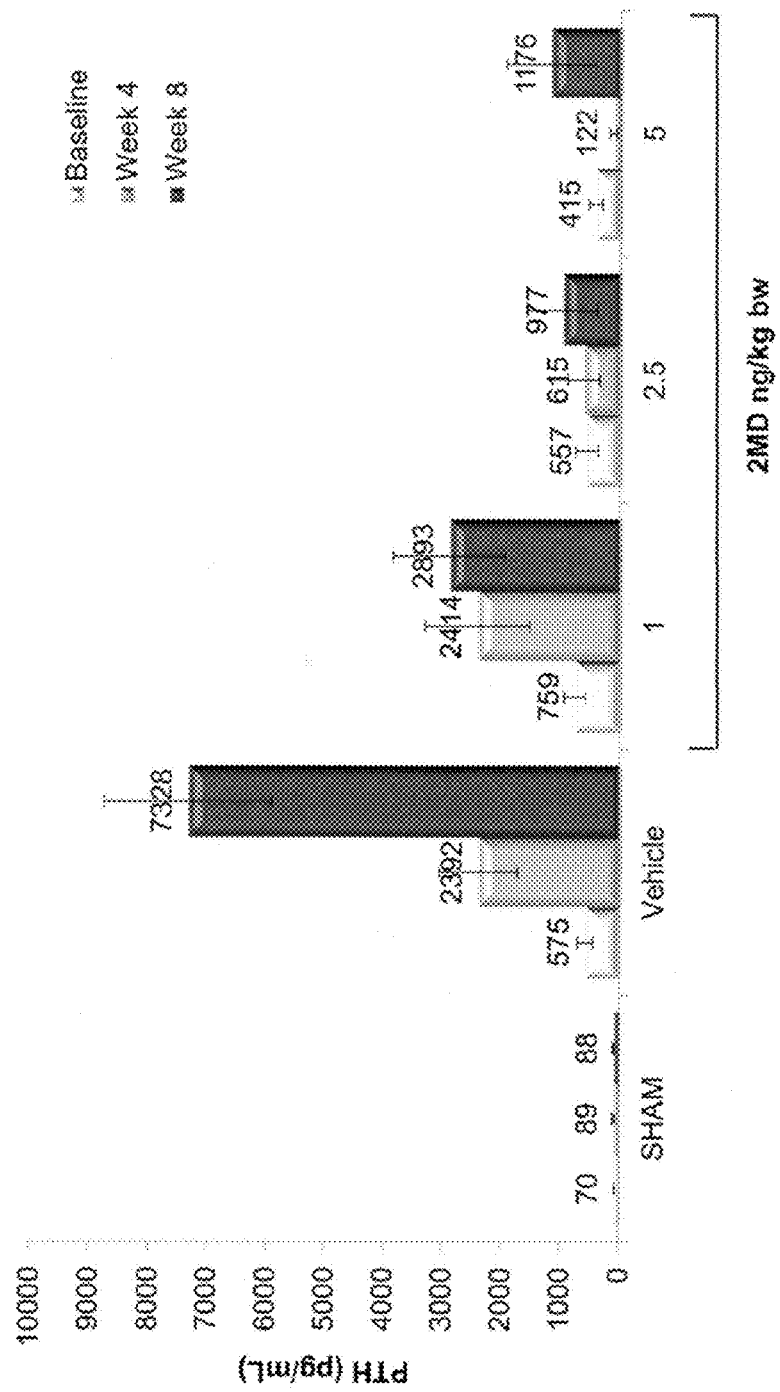
FIG. 5 is a graph illustrating the effect of oral administration of 2MD at various doses on serum PTH in a uremic rat model.
Figure 6:
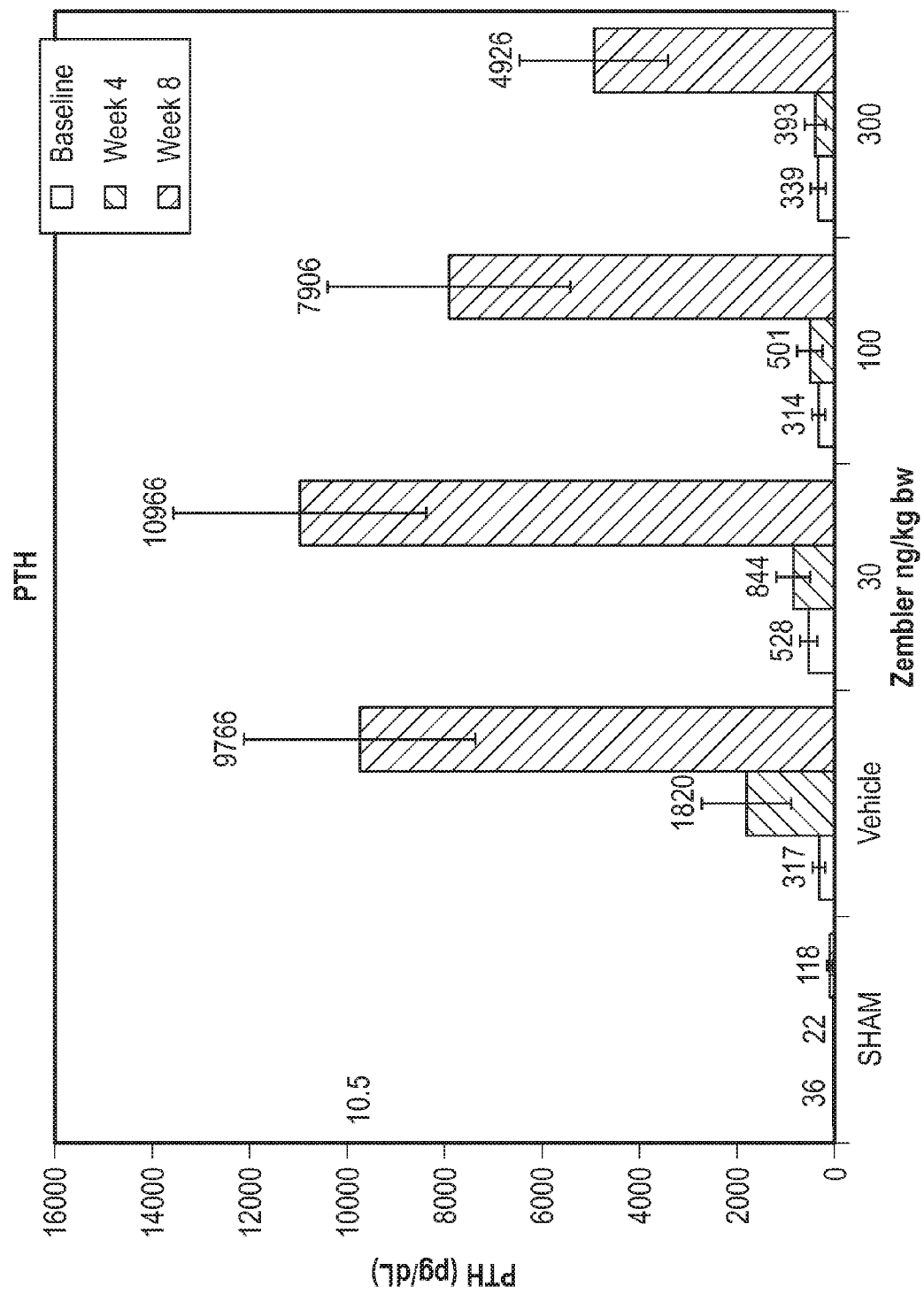
FIG. 6 is a graph illustrating the effect of oral administration of 19-nor-1α,25-dihydroxyvitamin $D_2$ (marketed under the tradename Zemplar®) at various doses on serum PTH in a uremic rat model.
Figure 7:
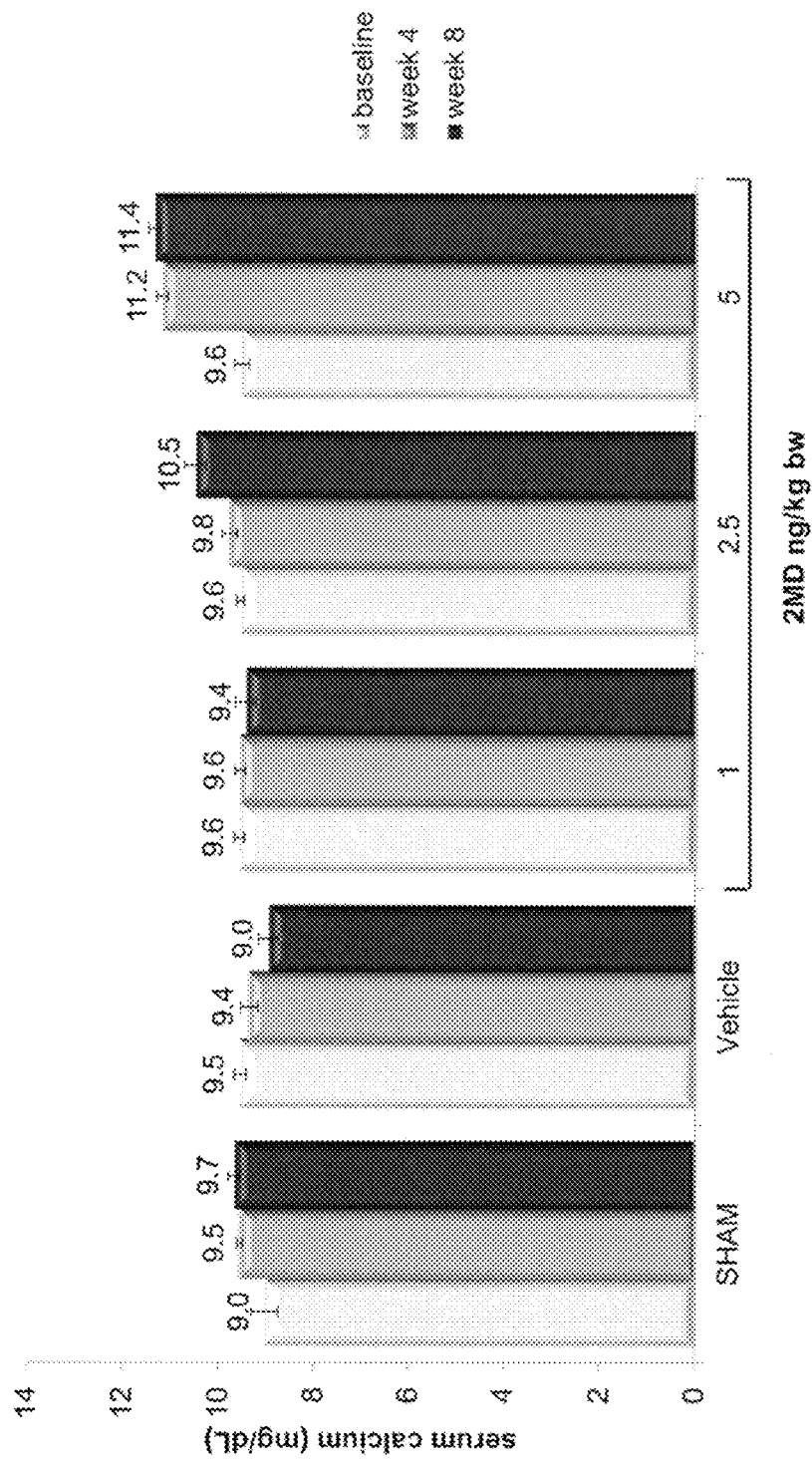
FIG. 7 is a graph illustrating the effect of oral administration of 2MD at various doses on serum calcium in a uremic rat model.
Figure 8:
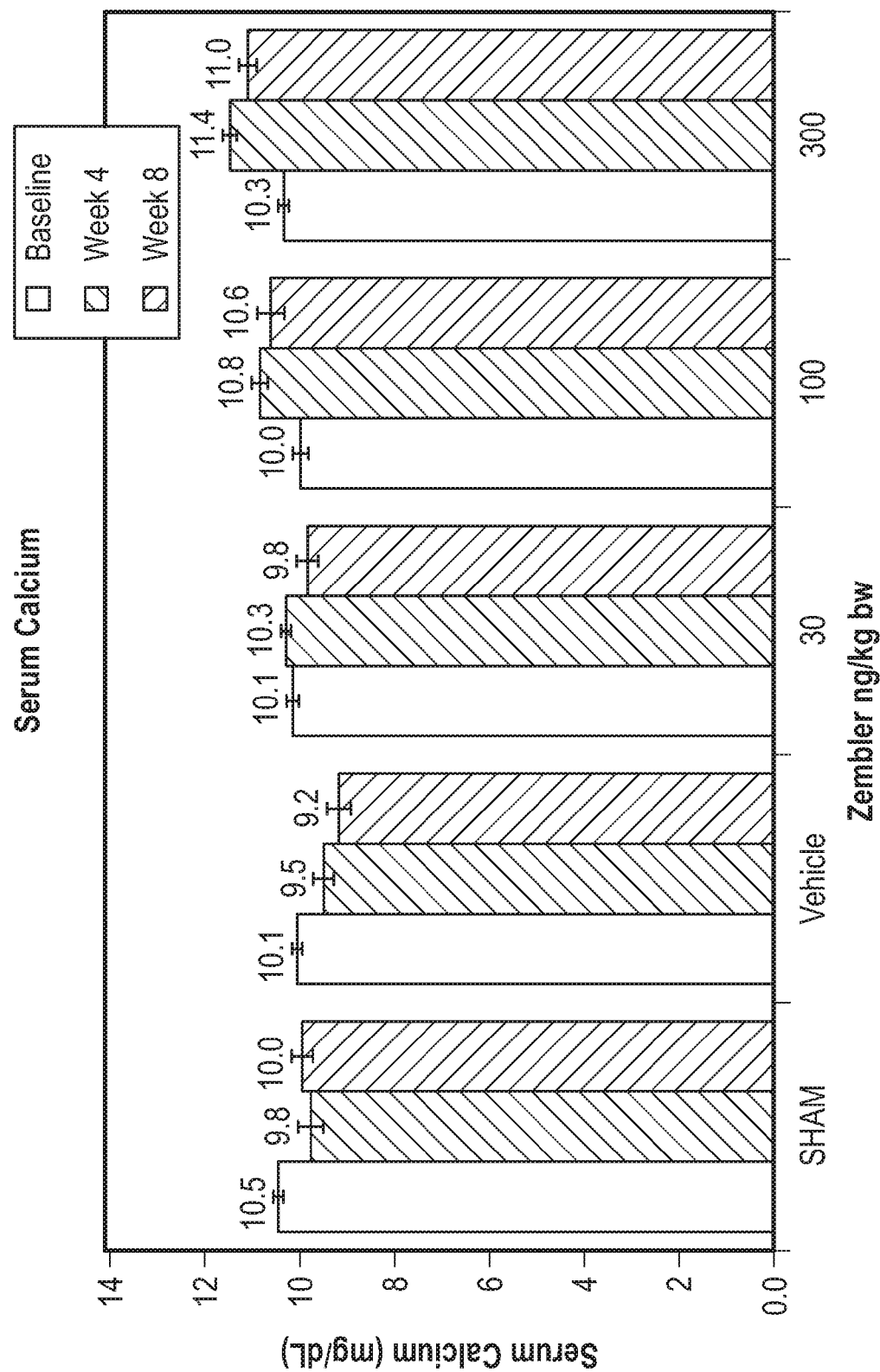
FIG. 8 is a graph illustrating the effect of oral administration of 19-nor-1α,25-dihydroxyvitamin $D_2$ (marketed under the tradename Zemplar®) at various doses on serum PTH in a uremic rat model.

FIG. 4 schematically illustrates the oral treatment protocol with 2MD. As shown in FIG. 5, oral administration of 2MD at daily doses of 1-5 ng/kg bw prevented an increase or effected a reduction in serum PTH levels. The observed effect lasted for eight weeks of therapy. As shown in FIG. 6, oral administration of Zemplar® at daily doses of 30-300 ng/kg bw prevented an increase in serum PTH levels, but the therapeutic effect was lost as the disease progressed. FIG. 7 illustrates that when orally administered clinically significant serum calcium increases are observed at 2MD doses of 5 ng/kg bw. FIG. 8 illustrates that when orally administered clinically significant serum calcium increases are observed at Zemplar® doses of 100 and 300 ng/kg bw.

Figure 9:
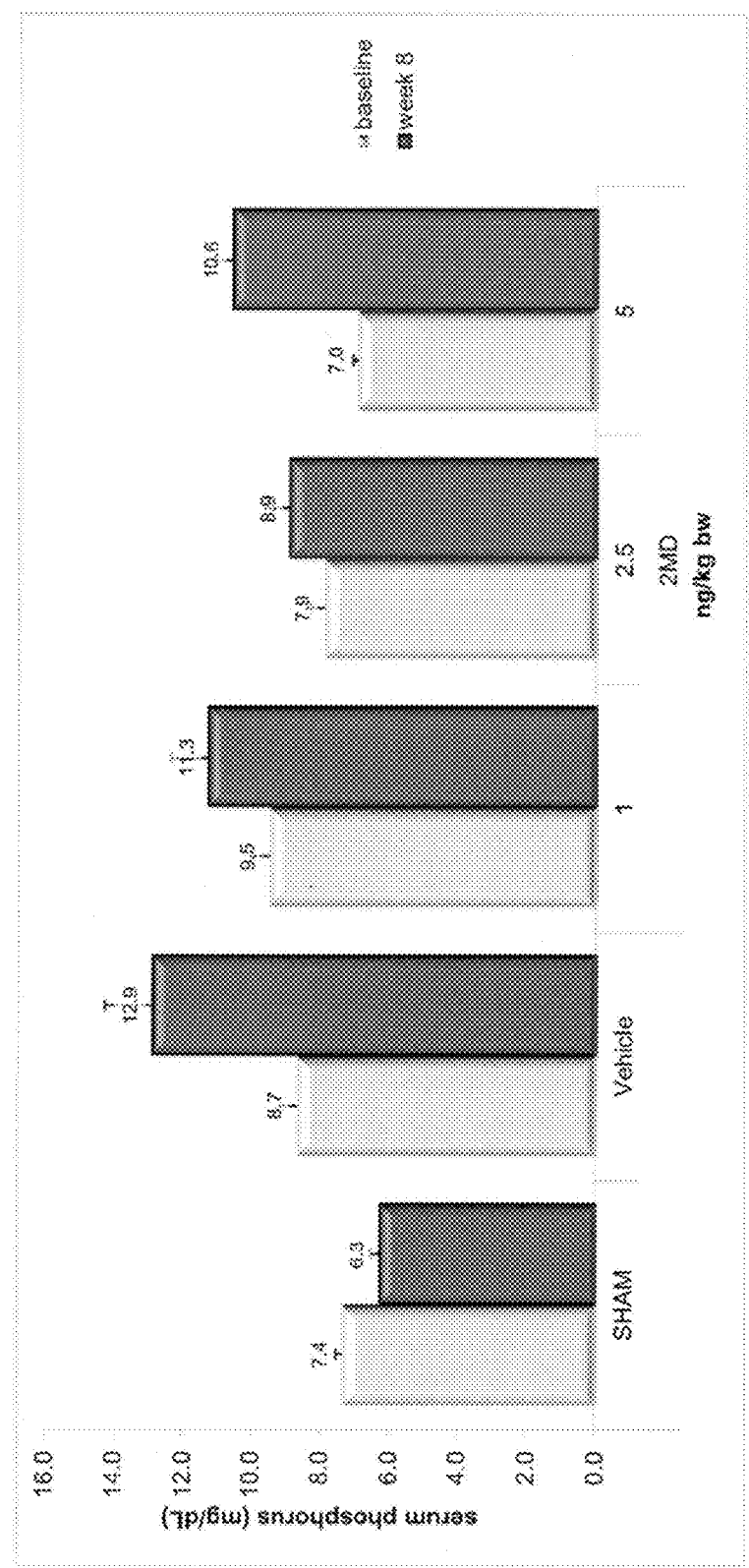
FIG. 9 is a graph illustrating the effect of oral administration of 2MD at various doses on serum phosphorus in a uremic rat model.
Figure 10:
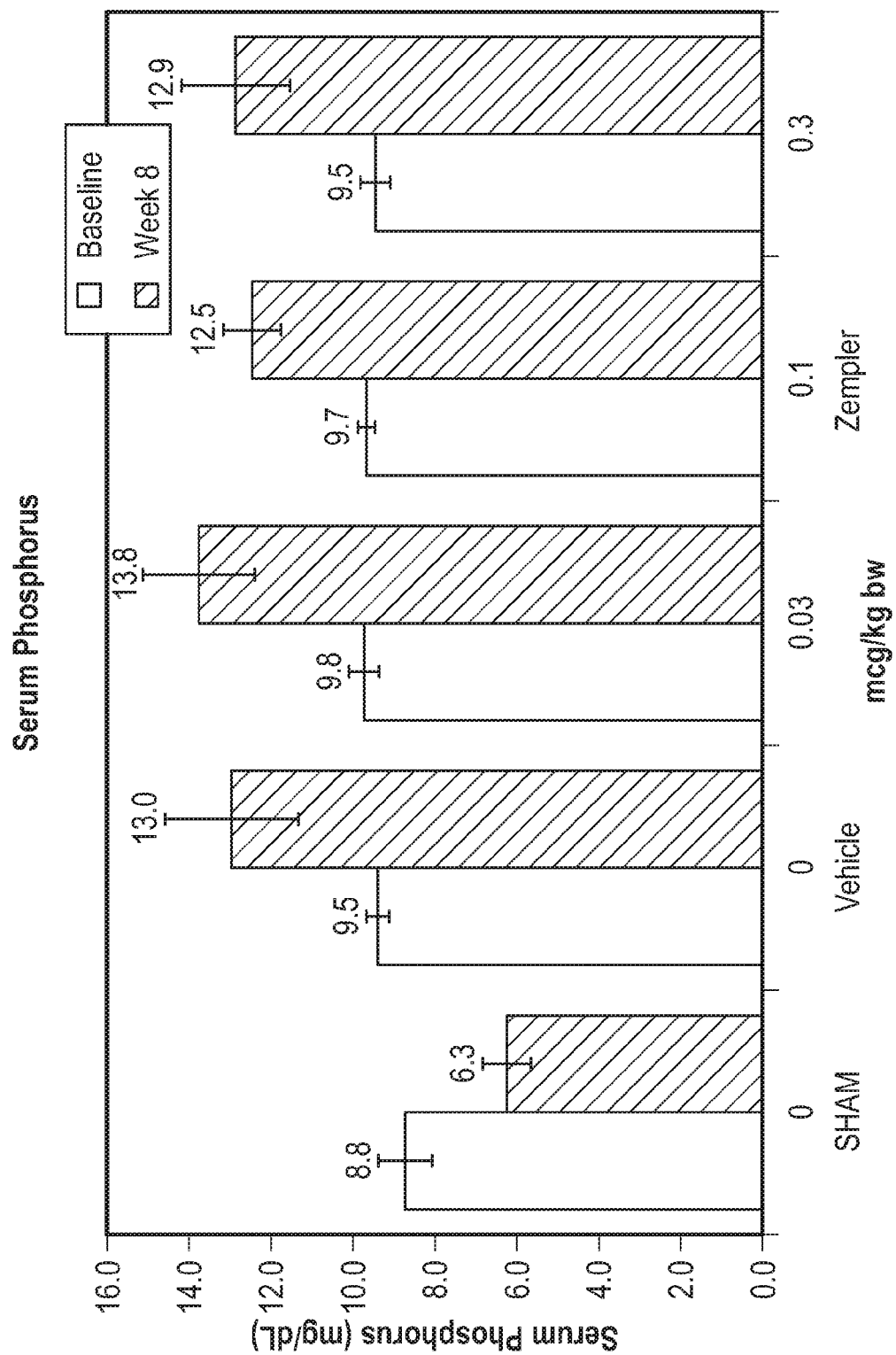
FIG. 10 is a graph illustrating the effect of oral administration of 19-nor-1α,25-dihydroxyvitamin $D_2$ (marketed under the tradename Zemplar®) at various doses on serum phosphorus in a uremic rat model.

As shown in FIG. 9, oral administration of 2MD at daily doses of 1-5 ng/kg bw reduced serum phosphorus levels in nephrectomized rats. In contrast, oral administration of Zemplar® did not reduce serum phosphorus levels in nephrectomized rats.

Figure 11:
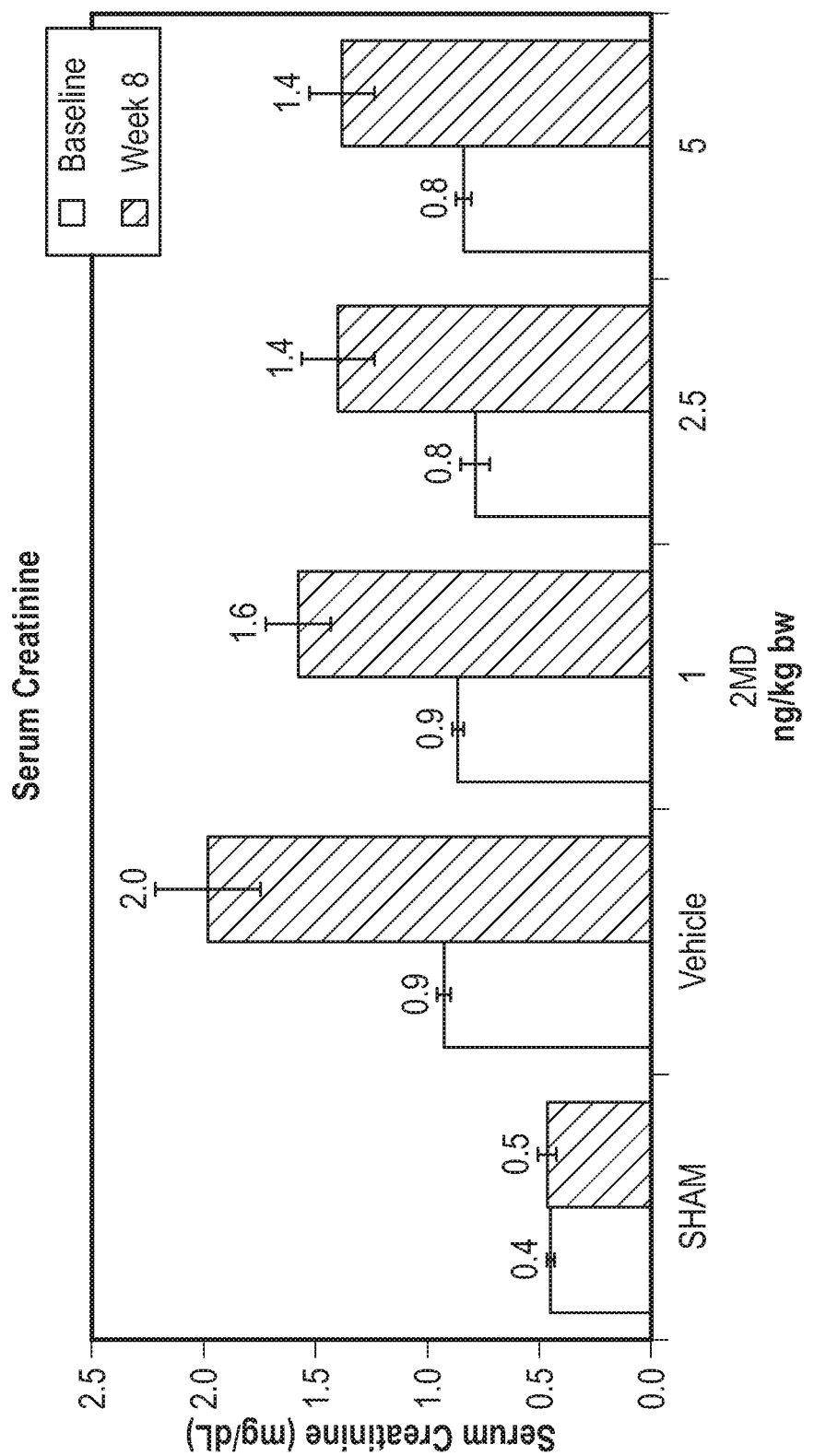
FIG. 11 is a graph illustrating the effect of oral administration of 2MD at various doses on serum creatinine in a uremic rat model.
Figure 12:
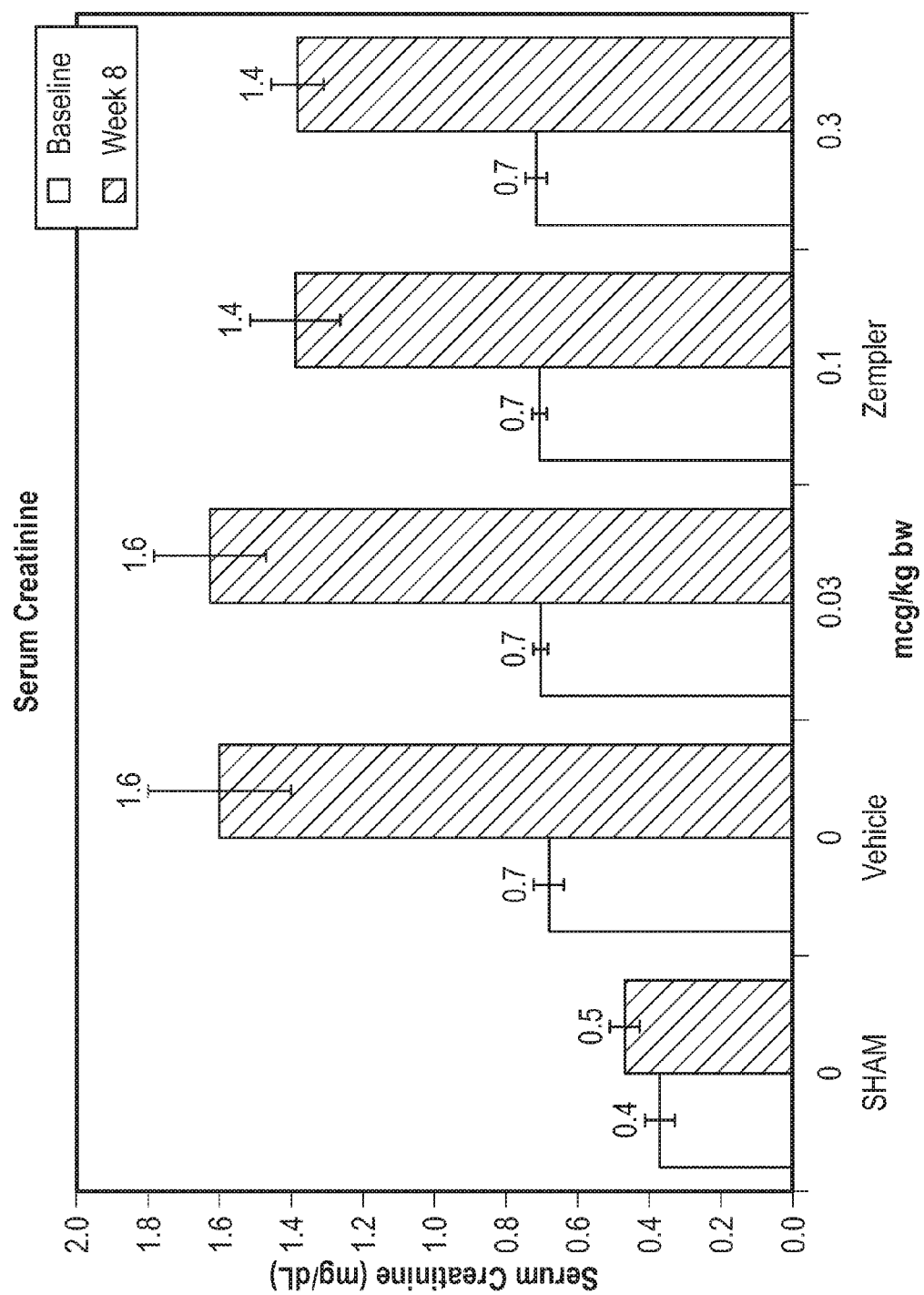
FIG. 12 is a graph illustrating the effect of oral administration of 19-nor-1α,25-dihydroxyvitamin $D_2$ (marketed wider the tradename Zemplar®) at various doses on serum creatinine in a uremic rat model.

As shown in FIG. 11, oral administration of 2MD at daily doses of 1-5 ng/kg bw resulted in lower serum creatinine levels compared to Vehicle control animals. In contrast, oral administration of Zemplar® lowered serum creatinine levels compared to Vehicle control animals, however, only at dose levels that significantly increased serum calcium.

Example 4

Phase 1B Trial—Oral Administration of 2MD to Postmenopausal Women

FIG. 13 illustrates the oral administration of 2MD once daily for 28 days to postmenopausal women at a dose of 110 nanograms (ng) reduced serum PTH levels by 21%, and a dose of 440 ng reduced serum PTH levels by 67%.

Inter itretation of Data

2MD or 2-methylene-19-nor-(20S)-1α,25-dihydroxyvitamin $D_3$ effectively reduces secondary hyperparathyroidism in a rat model of renal failure. Rats that have all but one sixth of their kidney mass surgically removed, and are placed on a high phosphorus diet will develop elevated PTH levels in the blood. Oral or intraperitoneal administration of 2MD on a daily or 3 times per week regimen will reduce the circulating levels of PTH. In addition, 2MD has the added benefit of preventing further increases or possibly reducing the levels of both phosphorus and creatinine in the blood. Furthermore, 2MD exhibits long-lasting effects in that rats treated orally for 8 weeks still show reduced PTH levels; whereas, other vitamin D compounds lose their effectiveness after 4 weeks of treatment in this animal model.

We claim:

1. A method of preventing an increase in serum parathyroid levels in a subject having secondary hyperparathyroidism, the method comprising administering a therapeutically effective amount of 2-methylene-19-nor-(20S)-1α,25-dihydroxyvitamin $D_3$ or pharmaceutically acceptable salts thereof to the subject without inducing hypercalcemia in the subject wherein an increase in serum parathyroid levels are prevented.

2. The method of claim 1, wherein the 2-methylene-19-nor-(20S)-1α,25-dihydroxyvitamin $D_3$ is formulated in an oral, topical, transdermal, parenteral, injection or infusion dosage form.

3. The method of claim 1, wherein the therapeutically effective amount ranges from about 1 ng/kg bw to about 10 ng/kg bw.

4. The method of claim 1, wherein the subject is receiving hemodialysis treatment.

5. The method of claim 4, wherein the subject is administered a therapeutically effective amount of 2-methylene-19-nor-(20S)-1α,25-dihydroxyvitamin $D_3$ three times per week.

6. The method of claim 1, wherein the subject has renal failure.

7. The method of claim 1, wherein the subject has a glomerular filtration rate of less than 15 mL/min/1.73 $m^2$.

* * * * *